(12) United States Patent
Schraga

(10) Patent No.: US 10,751,482 B2
(45) Date of Patent: Aug. 25, 2020

(54) PEN NEEDLE TIP

(71) Applicant: STAT MEDICAL DEVICES, INC., N. Miami, FL (US)

(72) Inventor: Steven Schraga, Surfside, FL (US)

(73) Assignee: STAT MEDICAL DEVICES, INC., N. Miami Beach, FL (US)

( * ) Notice: Subject to any disclaimer, the term of this patent is extended or adjusted under 35 U.S.C. 154(b) by 303 days.

(21) Appl. No.: 15/955,972

(22) Filed: Apr. 18, 2018

(65) Prior Publication Data

US 2018/0236177 A1 Aug. 23, 2018

Related U.S. Application Data

(63) Continuation of application No. 14/294,985, filed on Jun. 3, 2014, now abandoned, which is a continuation of application No. 13/564,428, filed on Aug. 1, 2012, now Pat. No. 8,834,415, which is a continuation of application No. 12/963,678, filed on Dec. 9, 2010, now Pat. No. 8,287,492, which is a continuation of application No. 11/616,195, filed on Dec. 26, 2006, now Pat. No. 7,871,397.

(51) Int. Cl.
*A61M 5/32* (2006.01)
*A61M 5/50* (2006.01)
*A61M 5/34* (2006.01)
*A61M 5/00* (2006.01)

(52) U.S. Cl.
CPC ........ *A61M 5/3213* (2013.01); *A61M 5/3204* (2013.01); *A61M 5/329* (2013.01); *A61M 5/347* (2013.01); *A61M 5/50* (2013.01); *A61M 5/002* (2013.01); *A61M 5/3202* (2013.01); *A61M 5/3216* (2013.01); *A61M 5/344* (2013.01)

(58) Field of Classification Search
CPC .. A61M 5/3204; A61M 5/3213; A61M 5/329; A61M 5/002; A61M 5/3202; A61M 5/3216; A61M 5/344; A61M 5/347; A61M 5/50; A61M 5/5086; A61M 5/321; A61M 5/34
See application file for complete search history.

(56) References Cited

U.S. PATENT DOCUMENTS

| 445,602 | A | 2/1891 | Richards |
| 4,894,055 | A | 1/1990 | Sudnak |
| 4,909,792 | A | 3/1990 | Norelli |
| 4,973,318 | A | 11/1990 | Holm et al. |

(Continued)

FOREIGN PATENT DOCUMENTS

| WO | 99/08742 | 2/1999 |
| WO | 2000/69501 | 11/2000 |
| WO | 2008/077706 A1 | 7/2008 |

*Primary Examiner* — Jason E Flick
(74) *Attorney, Agent, or Firm* — Thomas Horstemeyer, LLP

(57) ABSTRACT

A needle tip assembly for a pre-loaded syringe or a pen needle injection device, the needle tip assembly including a body comprising a double-ended needle and being installable and removable from the pre-loaded syringe or pen needle injection device. A needle cap is configured to cover a skin puncturing end of the double-ended needle and is removable to exposed the skin puncturing end. An outer safety member has a first portion that surrounds the body and a second portion that surrounds the skin puncturing end.

20 Claims, 40 Drawing Sheets

(56) References Cited

U.S. PATENT DOCUMENTS

| | | |
|---|---|---|
| 5,242,401 A | 9/1993 | Colsky |
| 5,242,416 A | 9/1993 | Hutson |
| 5,389,085 A | 2/1995 | D'Alessio et al. |
| 5,419,773 A | 5/1995 | Rupp |
| 5,454,828 A * | 10/1995 | Schraga .............. A61B 5/15142 606/172 |
| 5,591,138 A | 1/1997 | Vaillancourt |
| 5,593,387 A | 1/1997 | Rupp |
| 5,611,786 A | 3/1997 | Kirchhofer et al. |
| 5,980,488 A | 11/1999 | Thorne |
| 6,117,108 A | 9/2000 | Woehr et al. |
| 6,287,278 B1 | 9/2001 | Woehr et al. |
| 6,379,333 B1 | 4/2002 | Brimhall et al. |
| 6,391,003 B1 | 5/2002 | Lesch, Jr. |
| 6,460,234 B1 | 10/2002 | Gianchandani |
| 6,470,754 B1 | 10/2002 | Gianchandani |
| 6,616,630 B1 | 9/2003 | Woehr et al. |
| 6,652,490 B2 | 11/2003 | Howell |
| 6,749,588 B1 | 6/2004 | Howell et al. |
| 6,855,129 B2 | 2/2005 | Jensen et al. |
| 7,125,397 B2 | 10/2006 | Woehr et al. |
| 7,214,211 B2 | 5/2007 | Woehr et al. |
| 7,264,613 B2 | 9/2007 | Woehr et al. |
| 7,462,168 B2 | 12/2008 | Stonehouse et al. |
| 7,540,858 B2 | 6/2009 | DiBiasi |
| 7,553,293 B2 | 6/2009 | Jensen et al. |
| 7,871,397 B2 | 1/2011 | Schraga |
| 2002/0004648 A1 | 1/2002 | Larsen et al. |
| 2002/0133122 A1 | 9/2002 | Giambattista et al. |
| 2003/0014018 A1 | 1/2003 | Giambattista et al. |
| 2003/0105431 A1 | 6/2003 | Howell |
| 2003/0195471 A1 | 10/2003 | Woehr et al. |
| 2004/0116856 A1 | 6/2004 | Woehr et al. |
| 2004/0186434 A1 | 9/2004 | Harding et al. |
| 2004/0204681 A1 | 10/2004 | Thoresen et al. |
| 2004/0220532 A1 | 11/2004 | Caizza |
| 2004/0236284 A1 | 11/2004 | Hoste et al. |
| 2004/0236288 A1 | 11/2004 | Howell et al. |
| 2005/0004532 A1 | 1/2005 | Woehr et al. |
| 2005/0038392 A1 | 2/2005 | DeSalvo |
| 2005/0080378 A1 | 4/2005 | Cindrich et al. |
| 2005/0107748 A1 | 5/2005 | Thorne et al. |
| 2005/0277881 A1 | 12/2005 | Sibbitt |
| 2005/0277895 A1 * | 12/2005 | Giambattista ......... A61M 5/002 604/198 |
| 2005/0283115 A1 | 12/2005 | Giambattista et al. |
| 2006/0229652 A1 | 10/2006 | Iio et al. |
| 2006/0264828 A1 | 11/2006 | Woehr et al. |
| 2007/0049868 A1 | 3/2007 | Woehr et al. |
| 2007/0083159 A1 | 4/2007 | Woehr et al. |
| 2007/0100297 A1 | 5/2007 | Woehr et al. |
| 2007/0129689 A1 | 6/2007 | Woehr et al. |
| 2007/0203458 A1 | 8/2007 | Tsubota |
| 2007/0255225 A1 | 11/2007 | Alchas |
| 2008/0108951 A1 | 5/2008 | Jerde et al. |
| 2008/0154192 A1 | 6/2008 | Schraga |
| 2008/0177237 A1 | 7/2008 | Stonehouse et al. |
| 2008/0177238 A1 | 7/2008 | Follman et al. |
| 2009/0069753 A1 | 3/2009 | Ruan et al. |
| 2010/0114035 A1 | 5/2010 | Schubert |
| 2010/0292654 A1 | 11/2010 | Schraga |
| 2011/0022001 A1 | 1/2011 | Wei |
| 2011/0077615 A1 | 3/2011 | Schraga |
| 2011/0106016 A1 | 5/2011 | Wei |
| 2011/0118667 A1 | 5/2011 | Zaiken et al. |
| 2011/0160675 A1 | 6/2011 | Ruan et al. |
| 2012/0016300 A1 | 1/2012 | Ruan |

* cited by examiner

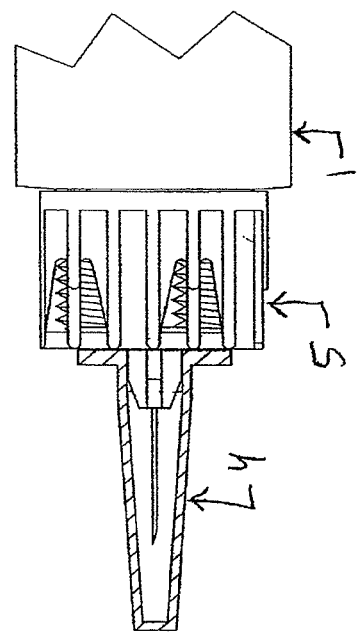
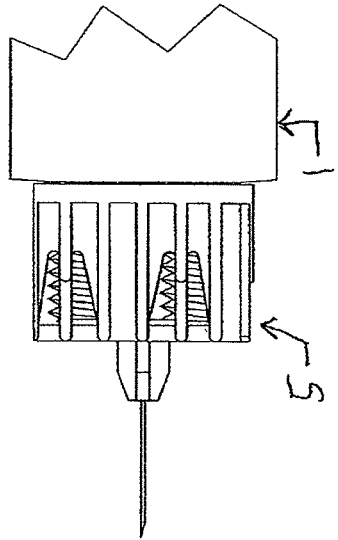
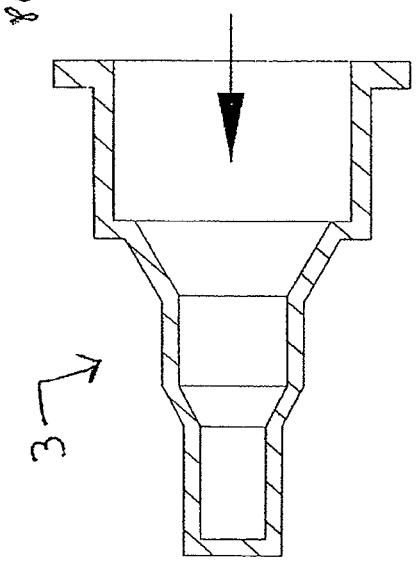
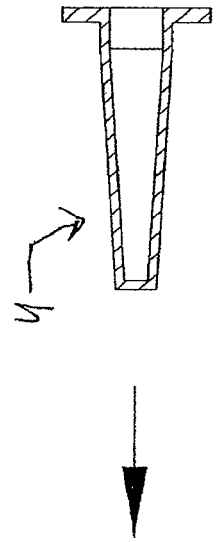
Fig. 4 PRIOR ART
Fig. 5 PRIOR ART

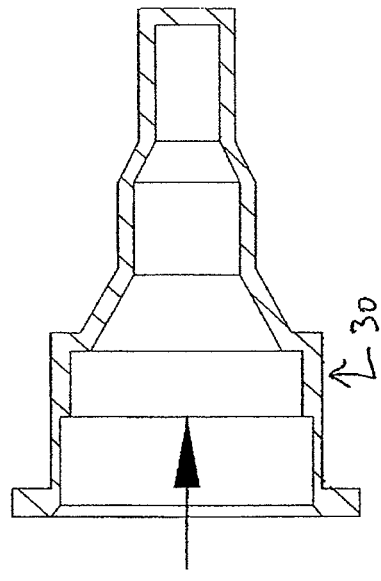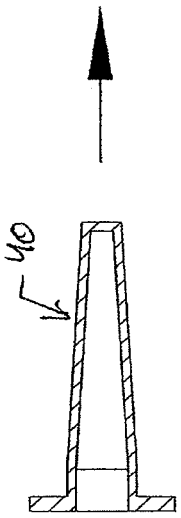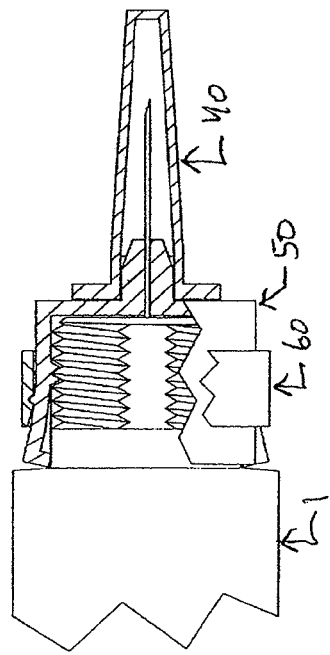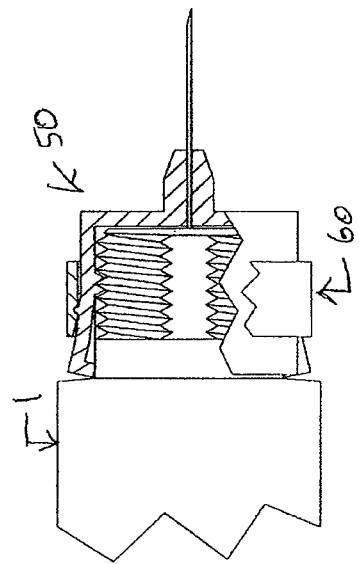
Fig. 11
Fig. 12

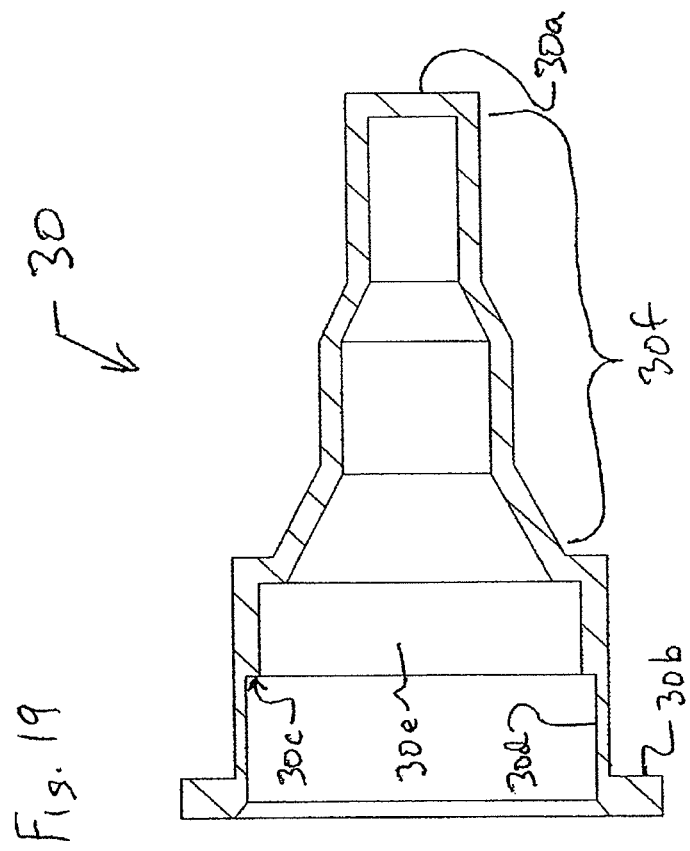
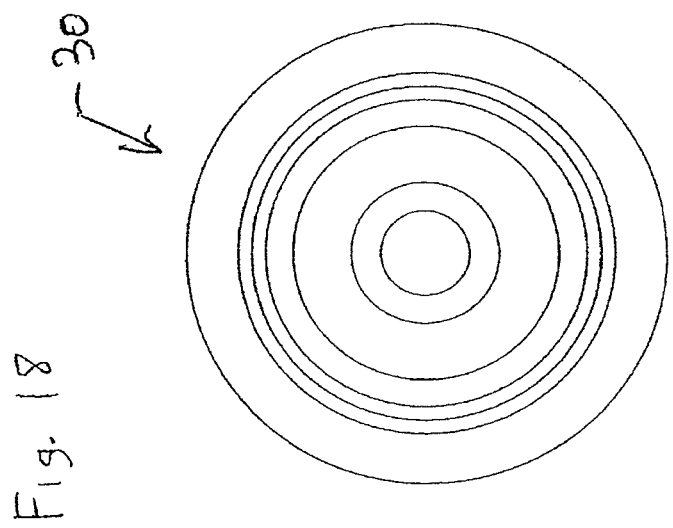

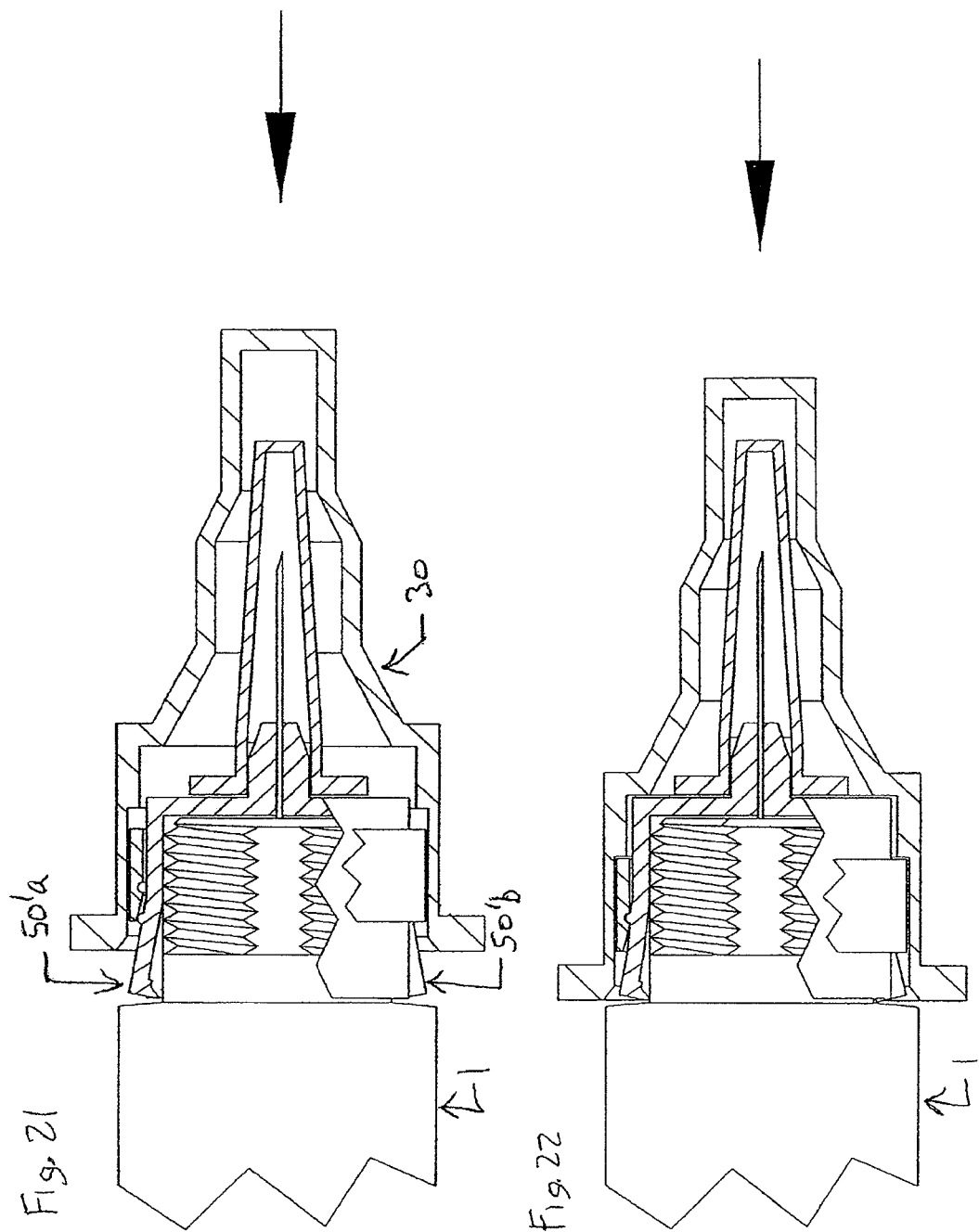

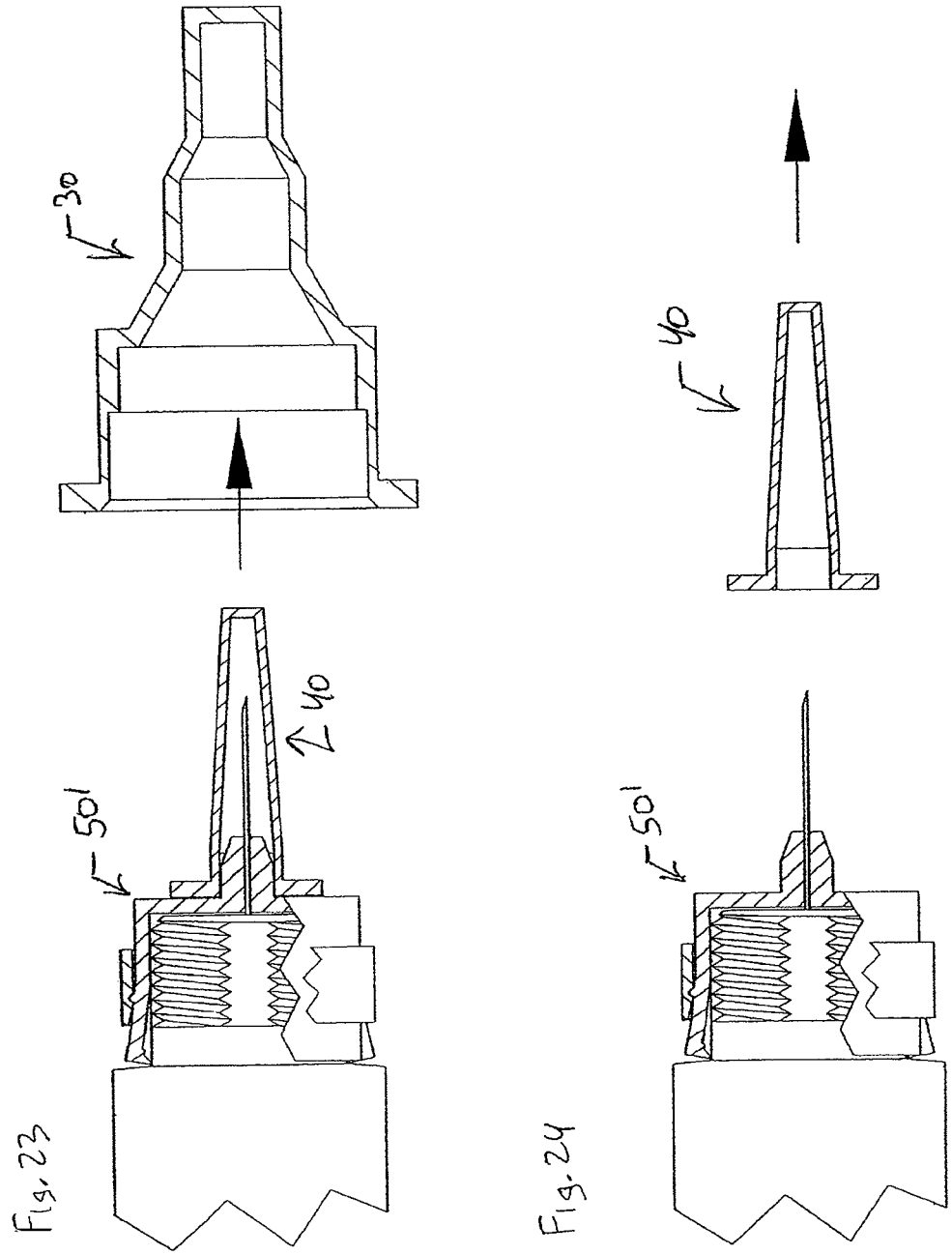

Fig. 27
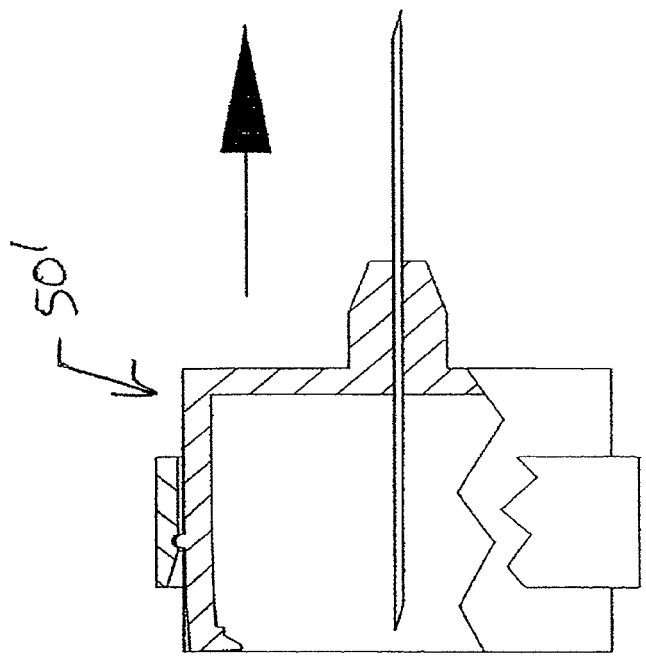
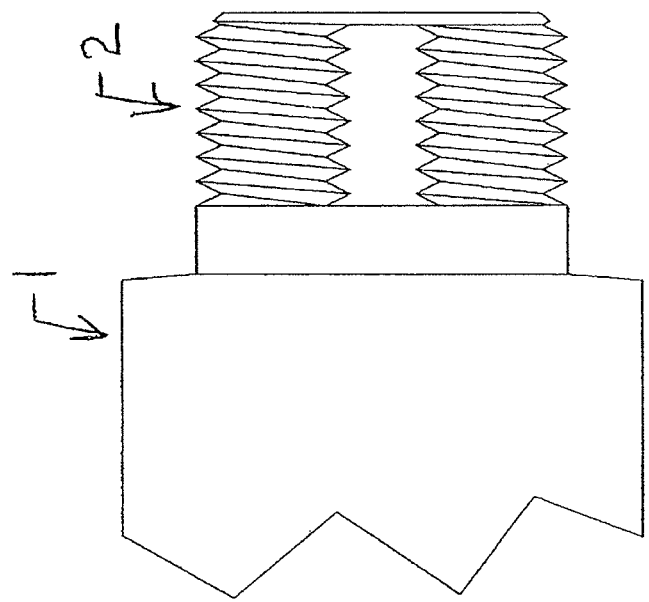

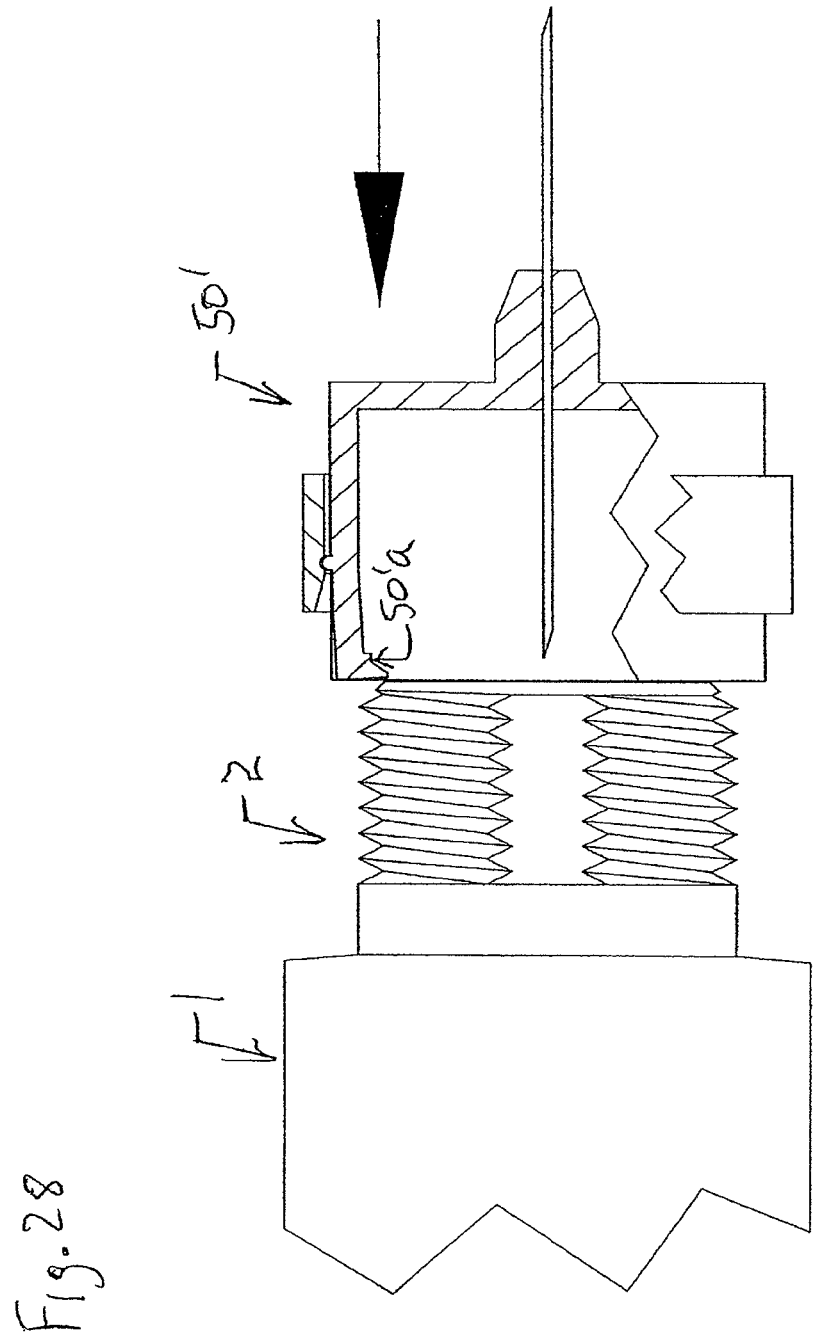

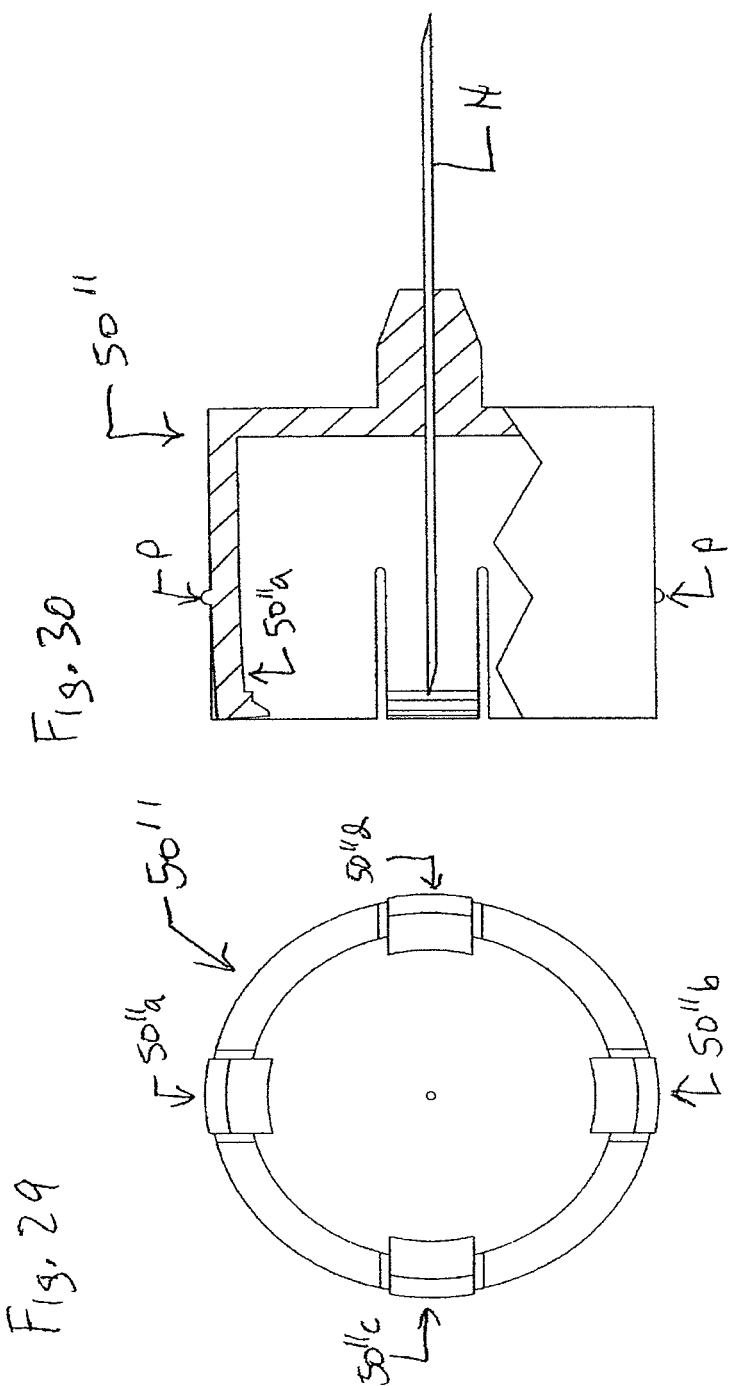

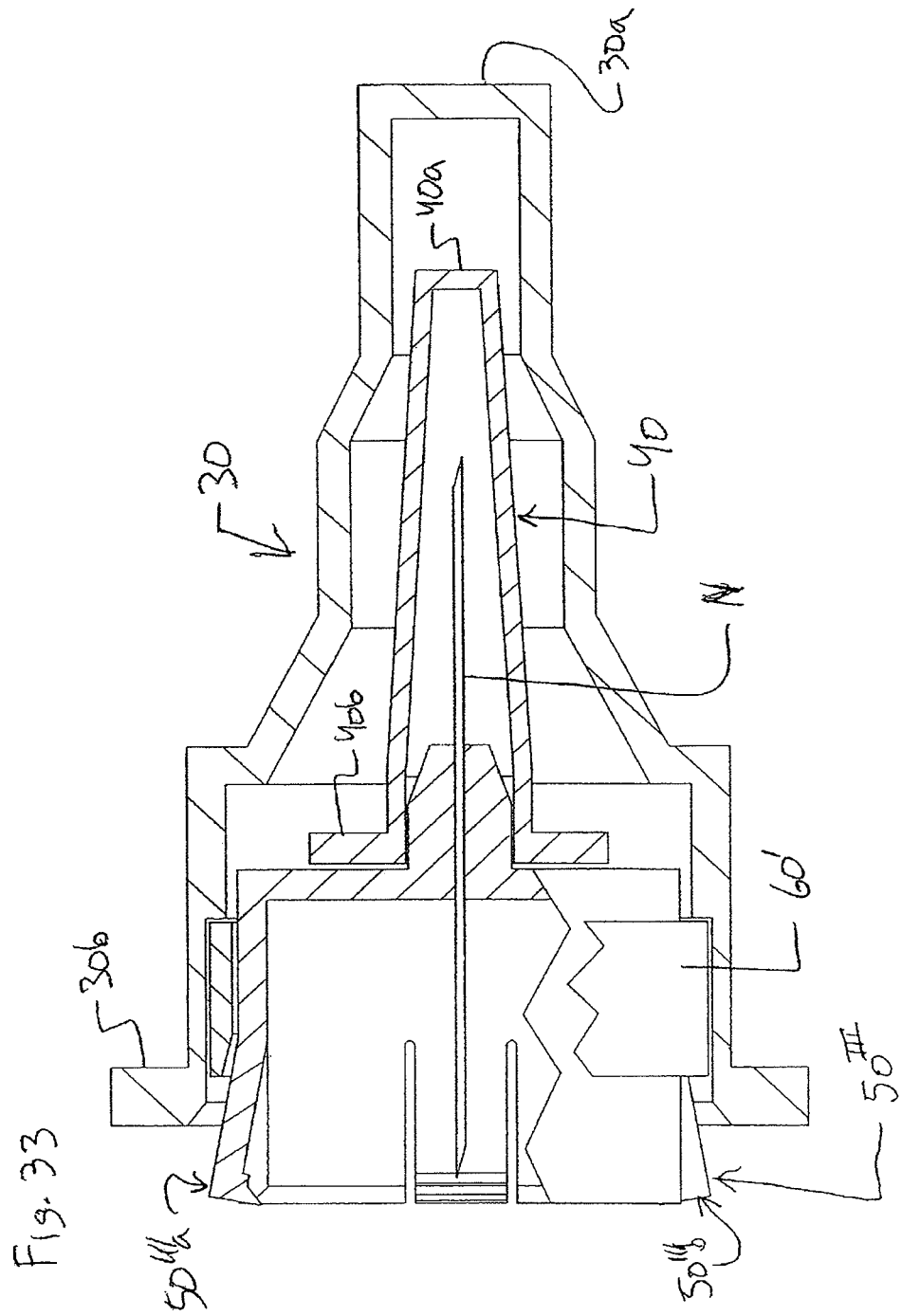

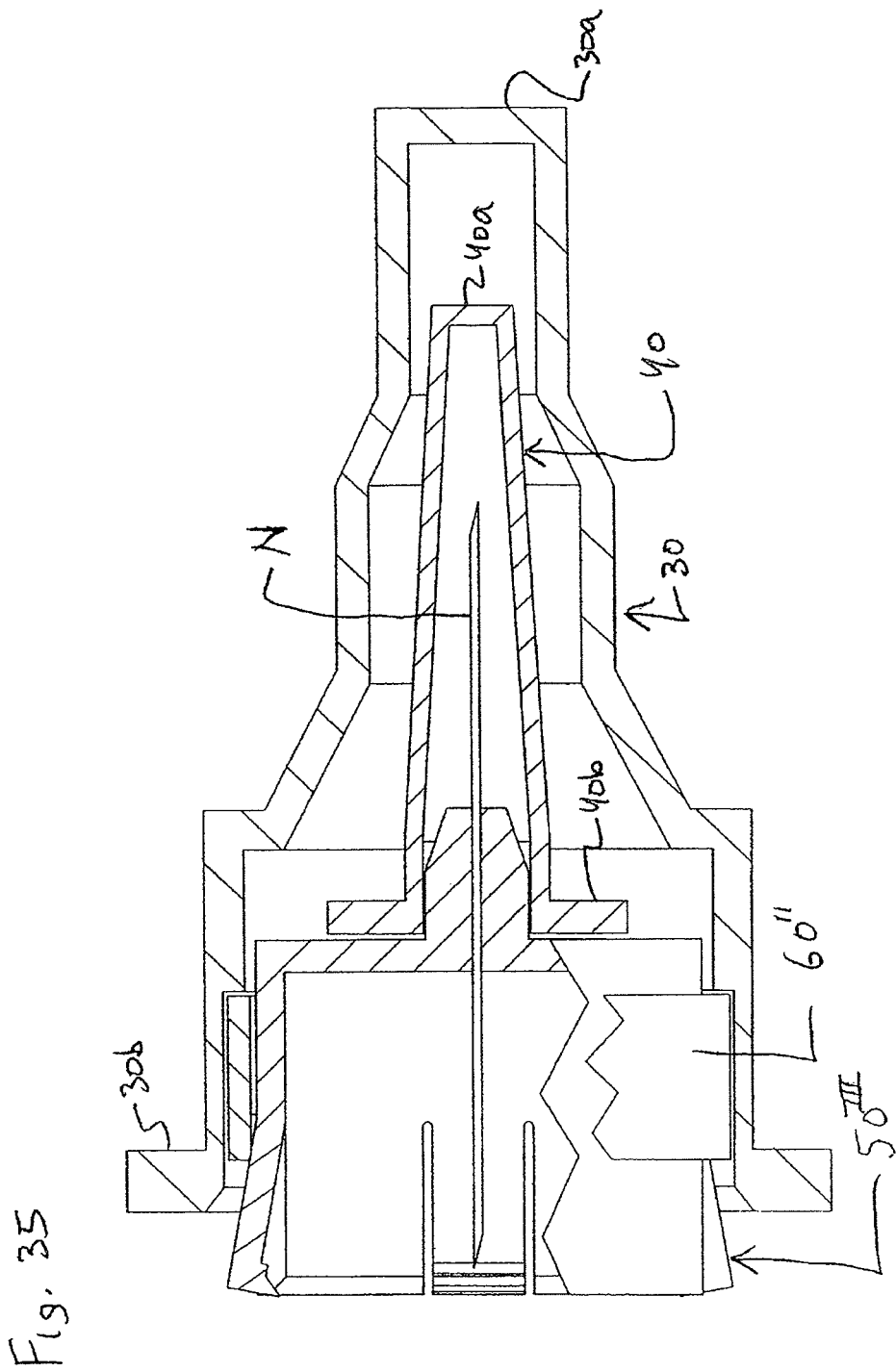

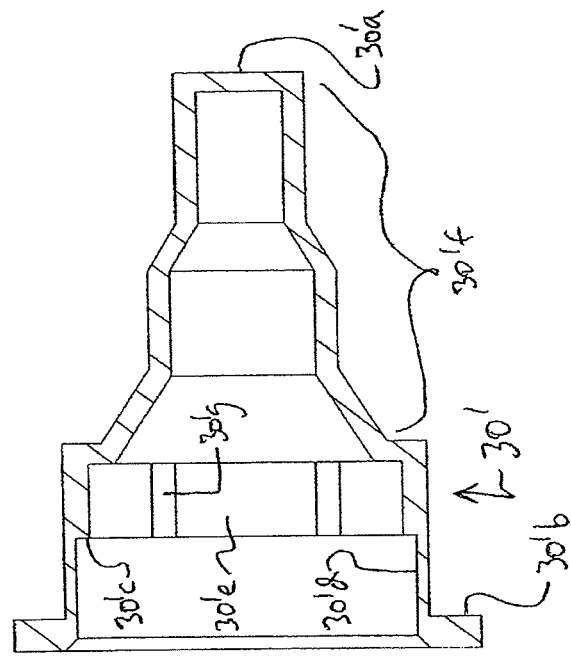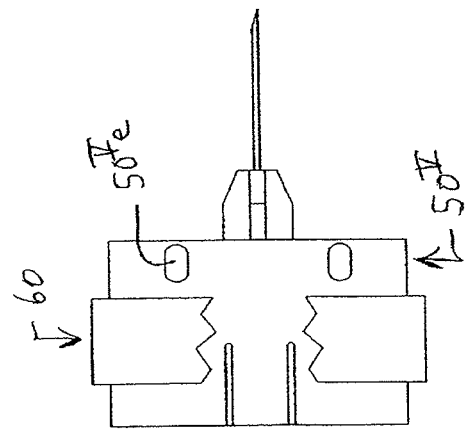

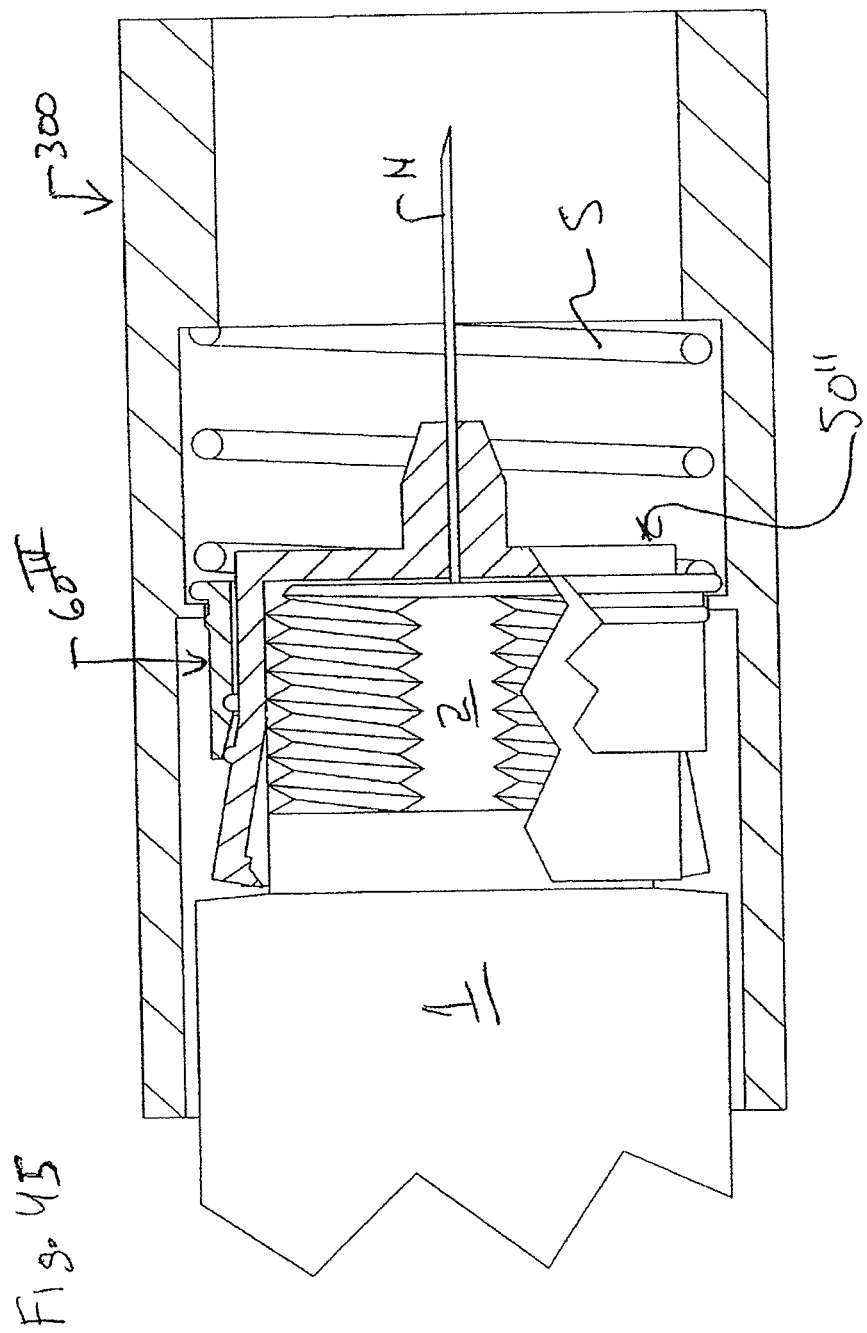

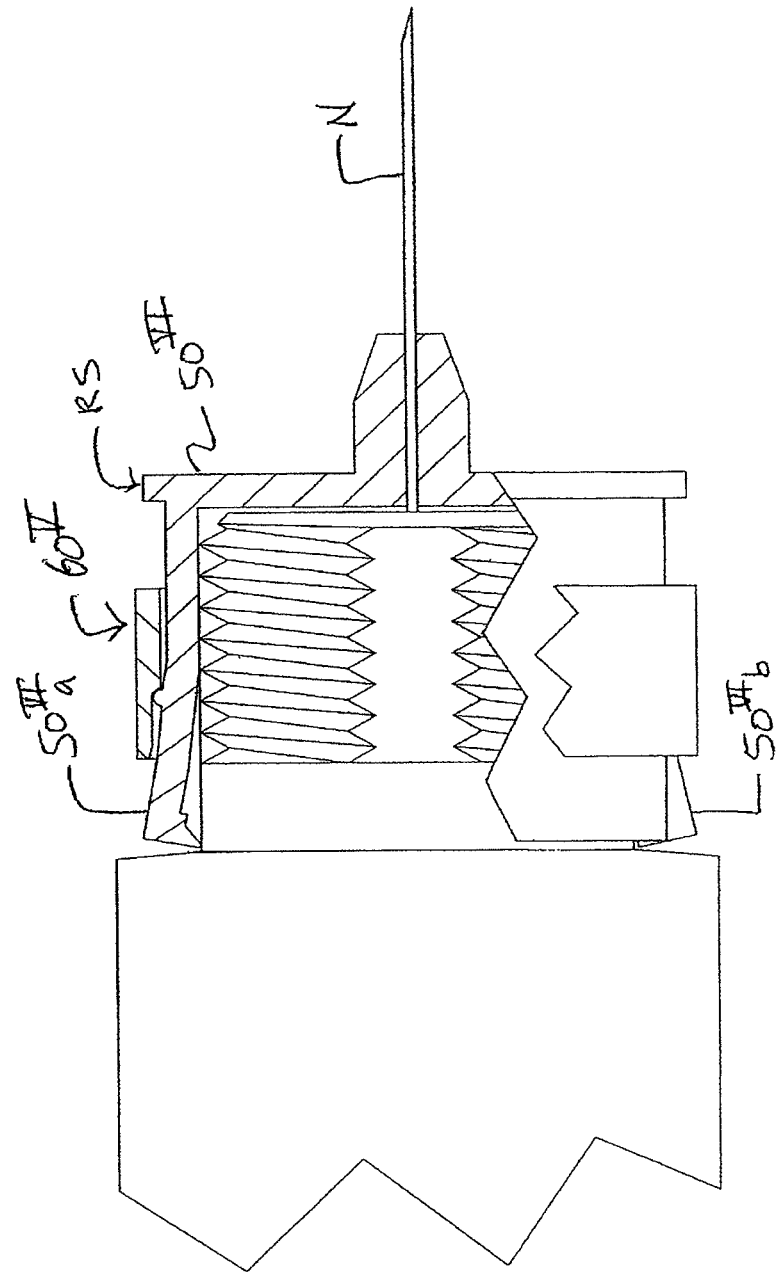

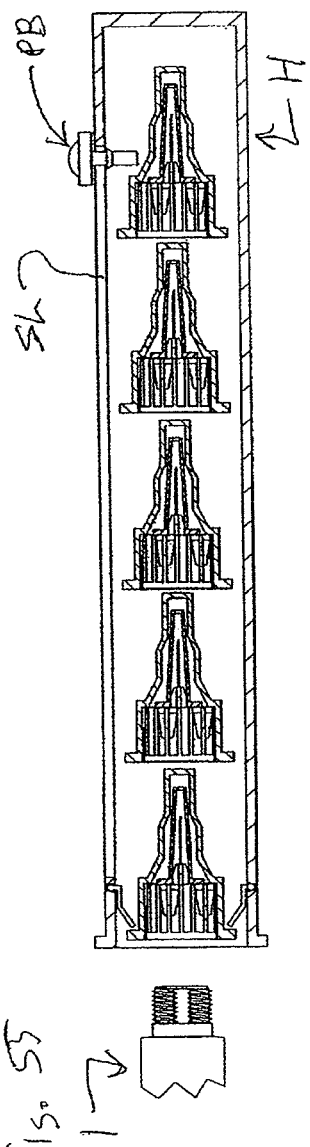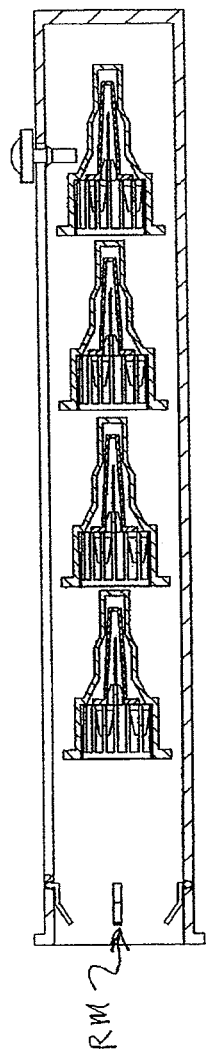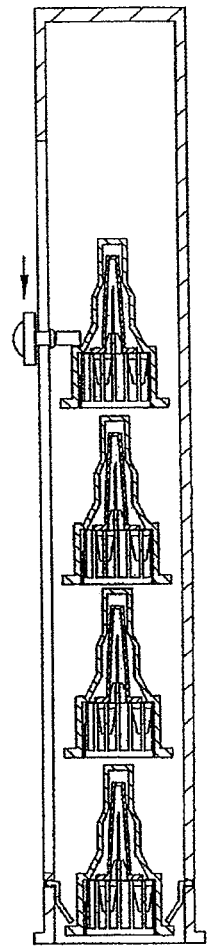

PEN NEEDLE TIP

CROSS-REFERENCE TO RELATED APPLICATIONS

The present application is a continuation of U.S. application Ser. No. 14/294,985 filed Jun. 3, 2014, which is a continuation of U.S. application Ser. No. 13/564,428 filed Aug. 1, 2012 and which issued as U.S. Pat. No. 8,834,415, which is a continuation of U.S. application Ser. No. 12/963,678 filed Dec. 9, 2010 and which issued as U.S. Pat. No. 8,287,492, which application is a continuation of U.S. application Ser. No. 11/616,195 filed Dec. 26, 2006 and which issued as U.S. Pat. No. 7,871,397. The disclosure of each of these applications is/are expressly incorporated by reference herein in its/their entireties.

BACKGROUND OF THE INVENTION

Field of the Invention

This invention relates generally to pen needles, e.g., pre-loaded syringes, such are utilized for injection of medicament into the body tissues of human and animal patients. More specifically, this invention relates to a pen needle having a removable tip which can be prevented from reuse and/or which utilizes one or more mechanisms for preventing the possibility of inadvertent needle pricks.

This invention also relates to pen needle tips for pen needles wherein the pen needle tip is configured to prevent it from being re-used.

This invention also relates to tips for devices such as, e.g., pre-loaded syringes, which can be used only once, i.e., single-use tips, and/or to tips which include one or more mechanisms for preventing the user from being pricked when handling the tip.

Discussion of Background Information

U.S. Pat. No. 4,973,318, the disclosure of which is hereby expressly incorporated by reference in its entirety, discloses a disposable syringe includes first and second housing elements which are coupled together for rotation without axial movement therebetween. The first housing element receives a cartridge of a solution to be injected, and mounts a liquid outlet needle at its front end. A piston rod is disposed in the second housing element to move axially therein, and this piston rod includes a rod element and a nut element. The rod element is coupled to the first housing element to move axially therein without relative rotation therewith, and the nut element is threaded to the rod element for telescoping movement therewith and is configured to move axially in the second housing element without relative rotation therein. A pressure receiving element is mounted on the nut element. The housing, rod, nut and pressure receiving elements cooperate such that relative rotation between the housing elements in a selected direction causes relative rotation between the nut and rod elements and thereby increases the effective length of the piston rod and causes the pressure receiving element to extend from the second housing element. A protective cap is removably mounted over the first housing element and is configured to abut second housing element while mounted in place on the first housing element. This protective cap is engaged with the first housing element such that rotation of the cap with respect to the second housing element causes rotation of the first housing element with respect to the second housing element.

This type of syringe is shown in FIGS. 1-7 wherein the pre-loaded syringe 1 has a proximal threaded end 2 which is configured to accept a needle tip assembly consisting of a needle tip 5, a needle tip cover 3, and a needle cover 4. As is evident from FIGS. 2 and 3, a user installs the needle tip assembly 3/4/5, after removing the assembly from its individual package, onto the threaded proximal end 2 by simply sliding it onto the end 2 axially. Because internal threads of the needle tip 5 are mounted to radially deflectable members, installation over threads of the end 2 occurs with a ratchet effect. This installation is made safe by the covers 4 and 5 which ensure that the user will not be pricked by the needle N. Once installed, the user can remove the needle tip cover 3 by simply sliding it off axially as is shown in FIG. 4. Next, as shown in FIG. 5, the user can remove the needle cover 4 to expose the needle N. The pen needle device then assumes the position shown in FIG. 6 and is made ready for use in providing an injection to the user. After injection, the user will typically remove the needle tip 5 and discard the same. To accomplish the removal, the user will typically reinstall the needle tip cover 3 and rotate it to cause the needle tip to unthread from the threaded end 2 (some users may even install the needle cover 4 prior to installing the cover 3). Once removed, however, it is still possible to reinstall the used needle tip 5 by simply repeating the steps noted above. FIG. 7 illustrates that the needle tip 5 can even be installed without the needle covers 3 and 4. Unless the user discards the needle tip 5, it is possible that she or other users will not remember or know that it has already been used. That is, there is nothing to prevent reuse of the needle tip 5 should someone attempt to reinstall the needle tip onto the end 2. Furthermore, if the user is unable to locate the covers 3 and 4 (i.e., if they have become lost), she must then attempt to grip the needle tip 5 in order to unthread it from the end 2. As is apparent, this action can be risky because the user can possibly inadvertently be pricked by the needle N either in attempting to properly grip the needle tip 5, in the action of rotating it to the point it is removed, or even in the handling of the needle tip 5 after it has been removed and prior to being properly discarded. Still further, if the needle tip 5 is not properly discarded (such as being correctly placed in a sharps container), others may come in contact with the needle tip 5 and possibly become injured thereby.

It is therefore desirable to provide a pen needle system which is safer to use compared to the conventional devices discussed above and/or which does not have one or more of the above-noted disadvantageous.

SUMMARY OF THE INVENTION

According to one non-limiting embodiment of the invention, there is provided a pen needle having a removable tip which can be prevented from reuse and/or which utilizes one or more mechanisms for preventing the possibility of inadvertent needle pricks.

According to another non-limiting embodiment of the invention, there is provided a pen needle tip for a pen needle wherein the pen needle tip is configured to prevent it from being re-used.

According to another non-limiting embodiment of the invention, there is provided a needle tip for a device such as, e.g., a pre-loaded syringe, which can be used only once, i.e., single-use tips, and/or to tips which include one or more mechanisms for preventing the user from being pricked when handling the tip.

According to another non-limiting embodiment of the invention, there is provided a pre-loaded syringe or pen needle injection device tip assembly comprising a needle tip comprising a body and a needle having a first puncturing end projecting out beyond a forward end of the body and a second puncturing end projecting into an interior space of the body. The interior space of the body is sized and configured to receive therein one end of the pre-loaded syringe or the pen needle injection device. A generally cylindrical sidewall of the body includes a slot oriented parallel to the needle. The second puncturing end being sized and configured to extend into the one end when the body is installed on the one end. The needle tip is structured and arranged to be removably connected to the one end of the pre-loaded syringe or the pen needle injection device.

According to another non-limiting embodiment of the invention, there is provided a needle tip assembly comprising a needle tip, a needle tip cover structured and arranged to facilitate installation of the needle tip onto at least one of a pen needle, a pre-loaded syringe, and an injection device, and at least one of an arrangement for preventing re-installation or re-use of the needle tip, a safety mechanism coupled to the needle tip via a living hinge, and a safety cover non-removably coupled to the needle tip.

The arrangement may comprise a ring which is movable from a first position to a second position. The arrangement may comprise a ring which is axially movable. The arrangement may comprise a locking member which is movable from an unlocked position to a locked position. The arrangement may comprise a movable member mounted to a body of the needle tip, wherein the movable member is axially movable from a first position to a second position by the needle tip cover. The arrangement may comprise a movable member mounted to a body of the needle tip, wherein the movable member is axially movable from a first position to a second position, and wherein, when in the second position, the needle tip is prevented from being re-installed. The arrangement may comprise an elastic member mounted to a body of the needle tip, wherein the elastic member is movable from a first position to a second position, and wherein, when in the second position, the needle tip is prevented from being re-installed. The arrangement may comprise at least one inwardly projecting member adapted to be deflected inwardly. The at least one inwardly projecting member may be biased away from inward deflection. The arrangement may further comprise a ring which is movable from a first position to a second position causing inward deflection of the at least one inwardly projecting member. The arrangement may further comprise a ring which is axially movable to a position causing inward deflection of the at least one inwardly projecting member. The arrangement may further comprise a locking member which is movable from an unlocked position to a locked position causing inward deflection of the at least one inwardly projecting member. The arrangement may further comprise a movable member mounted to a body of the needle tip, wherein the movable member is axially movable from a first position to a second position by the needle tip cover, whereby the second position causes inward deflection of the at least one inwardly projecting member. The arrangement may further comprise a movable member mounted to a body of the needle tip, wherein the movable member is axially movable from a first position to a second position, and wherein, when in the second position, the needle tip is prevented from being re-installed by inward deflection of the at least one inwardly projecting member. The arrangement may further comprise an elastic member mounted to a body of the needle tip, wherein the elastic member is movable from a first position to a second position, and wherein, when in the second position, the needle tip is prevented from being re-installed by inward deflection of the at least one inwardly projecting member. The safety mechanism may comprise a proximal needle cover. The safety mechanism may comprise a member which covers a distal end of the needle tip. The safety cover may comprise a proximal needle cover. The safety cover may comprise a member which covers a distal end of the needle tip. The needle tip cover may be structured and arranged to facilitate removal of the needle tip from the at least one of the pen needle, the pre-loaded syringe, and the injection device.

According to another non-limiting embodiment of the invention, there is provided a needle tip assembly comprising a needle tip comprising a body and a needle projecting from the body and a needle tip cover structured and arranged to facilitate installation of the needle tip onto at least one of a pen needle, a pre-loaded syringe, and an injection device, wherein the needle tip cover activates an arrangement for preventing re-installation or re-use of the needle tip.

The assembly may further comprise at least one of a safety mechanism coupled to the needle tip via a living hinge and a safety cover non-removably coupled to the needle tip. The needle tip cover may be structured and arranged to facilitate removal of the needle tip from the at least one of the pen needle, the pre-loaded syringe, and the injection device.

According to another non-limiting embodiment of the invention, there is provided a needle tip assembly comprising a needle tip comprising a body, a needle projecting from the body, and at least one inwardly projecting member adapted to be deflected inwardly and a needle tip cover structured and arranged to facilitate installation of the needle tip onto at least one of a pen needle, a pre-loaded syringe, and an injection device, wherein, when the at least one inwardly projecting member is deflected inwardly, the needle tip is prevented from being re-installed.

The needle tip cover may activate an arrangement for preventing re-installation or re-use of the needle tip. The assembly may further comprise at least one of a safety mechanism coupled to the needle tip via a living hinge and a safety cover non-removably coupled to the needle tip. The needle tip cover may be structured and arranged to facilitate removal of the needle tip from the at least one of the pen needle, the pre-loaded syringe, and the injection device. The assembly may further comprise an arrangement that is movable from a first position to a second position. The arrangement may comprise a ring which is axially movable. The arrangement may comprise a locking member which is movable from an unlocked position to a locked position. The arrangement may comprise a movable member mounted to the body of the needle tip, wherein the movable member is axially movable from a first position to a second position by the needle tip cover. The arrangement may comprise a movable member mounted to the body of the needle tip, wherein the movable member is axially movable from a first position to a second position, and wherein, when in the second position, the needle tip is prevented from being re-installed. The arrangement may comprise an elastic member mounted to the body of the needle tip, wherein the elastic member is movable from a first position to a second position, and wherein, when in the second position, the needle tip is prevented from being re-installed.

According to another non-limiting embodiment of the invention, there is provided a method of using the needle tip assembly of the type described above, wherein the method comprises installing the needle tip assembly onto a proximal end of an injection device, activating the arrangement before using the injection device, and re-installing the needle tip cover and removing the needle tip using the needle tip cover.

According to another non-limiting embodiment of the invention, there is provided a method of using the needle tip assembly of the type described above, wherein the method comprises installing the needle tip assembly onto a proximal end of an injection device, activating with the needle tip cover, an arrangement for preventing re-installation or re-use of the needle tip, and re-installing the needle tip cover and removing the needle tip using the needle tip cover.

According to another non-limiting embodiment of the invention, there is provided a method of using the needle tip assembly of the type described above, wherein the method comprises installing the needle tip assembly onto a proximal end of an injection device and re-installing the needle tip cover and removing the needle tip using the needle tip cover, wherein after removal, the at least one inwardly projecting member is deflected inwardly so as to prevent re-installation of the needle tip.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 4 shows how the needle tip cap can be removed from the prior art needle tip assembly of FIG. 3;

FIG. 5 shows how the needle cap can be removed from the prior art needle tip of FIG. 4;

FIG. 11 shows the needle tip assembly of FIG. 10 as the needle tip cap is removed;

FIG. 12 shows the needle tip assembly of FIG. 11 as the needle cap is removed;

FIG. 18 shows a distal end view of the needle tip cap which can be used in the needle tip assembly according to the invention;

FIG. 19 shows a side cross-section view of the needle tip cap of FIG. 18;

FIG. 21 shows the needle tip assembly of FIG. 20 after installation onto the proximal end;

FIG. 22 shows the needle tip assembly of FIG. 21 after the needle tip cap is moved axially to a position which causes a ring to move to a locked position;

FIG. 23 shows the needle tip assembly of FIG. 22 as the needle tip cap is removed;

FIG. 24 shows the needle tip assembly of FIG. 23 as the needle cap is removed;

FIG. 27 shows the needle tip and proximal end of FIG. 26 after the needle tip is removed from the proximal end;

FIG. 28 shows how the inwardly deflecting members interfere with and/or prevent re-installation of the needle tip, i.e., the inwardly oriented projections have deflected inwardly to the point that they can no longer threadably engage with the threads of the proximal end and function to, in effect, reduce a diameter of the distal opening of the needle tip to the point that it is smaller than the outer diameter of the proximal end;

FIG. 29 shows a distal end of another needle tip which can be used in the embodiment of FIGS. 20-28. The lock ring has been removed for purposes of clarity. Unlike the embodiment of FIGS. 20-28 which utilizes two oppositely arranged inwardly deflecting members, this embodiment utilizes four equally spaced inwardly projecting members. As is evident from FIG. 29, the inwardly oriented projections have deflected inwardly to the point that they, in effect, reduce a diameter of the distal opening of the needle tip so that it is smaller than the outer diameter of the proximal end;

FIG. 30 shows a side partial cross-section view of the needle tip of FIG. 29;

FIG. 33 shows a needle tip assembly according to still another embodiment of the invention. The needle tip assembly is shown in a position prior to installation onto the proximal end. The needle tip is shown in partial cross-section while the needle tip cap and the needle cap are shown in cross-section. Unlike the previous embodiments shown in FIGS. 8-32, this embodiment utilizes a ring which does not lock when moved to a position causing the inwardly projecting members to deflect inwardly. As such, the needle tip does not include projections which would engage with a recess in the ring;

FIG. 35 shows a needle tip assembly according to still another embodiment of the invention. The needle tip assembly is shown in a position prior to installation onto the proximal end. The needle tip is shown in partial cross-section while the needle tip cap and the needle cap are shown in cross-section. Unlike the previous embodiments shown in FIGS. 8-32, this embodiment utilizes a ring which does not have a tapered distal end and does not lock to the needle tip when moved to a position causing the inwardly projecting members to deflect inwardly;

FIG. 39 shows a side view of a needle tip according to still another embodiment of the invention. The needle tip is similar to that shown in the embodiment of FIGS. 8-19 except that it utilizes mechanisms for transferring torque from the needle tip cap to the needle tip. These mechanisms have the form of projections formed on the needle tip which slidably engage with recesses formed within the needle tip cap;

FIG. 40 shows a side cross-section view of a needle tip cap which can be used with the needle tip shown in FIG. 39. The needle tip cap is similar to that shown in the embodiment of FIGS. 8-19 except that it utilizes mechanisms for transferring torque from the needle tip cap to the needle tip. These mechanisms have the form of recesses formed within the needle tip cap which slidably receive therein the projections formed on the needle tip;

FIG. 45 shows a needle tip assembly according to still another embodiment of the invention. The needle tip assembly is shown in a position after being installed onto the proximal end of the pen needle injection device. The needle tip is shown in partial cross-section while the needle tip cap and the needle cap are shown in cross-section. This embodiment is similar to the embodiment shown in FIGS. 41-44 except that it also includes a spring which biases the needle tip cap towards the original position;

FIG. 46 shows the pen needle device with a installed needle tip according to another non-limiting embodiment of the invention. This embodiment utilizes a ring which frictionally engages with projections of the needle tip without locking with the projections. In this position, the ring has been moved to the locked position which has caused a plurality of inwardly deflecting members to engage the threaded proximal end of the pen needle device;

FIG. 55 shows one non-limiting way in which a plurality of needle tip assemblies of either the prior art variety or those of the invention described herein can be packaged in a housing. The housing also functions as a tool for installing one needle tip assembly at a time onto the end of a pen needle;

FIG. 56 shows the housing after one of the needle tip assemblies has been installed onto the end of a pen needle; and FIG. 57 shows the housing after the user advances a push-button to move the needle tip assemblies to a position that readies it for installing another of the needle tip assemblies onto the end of a pen needle.

DETAILED DESCRIPTION OF THE INVENTION

Figure 1:
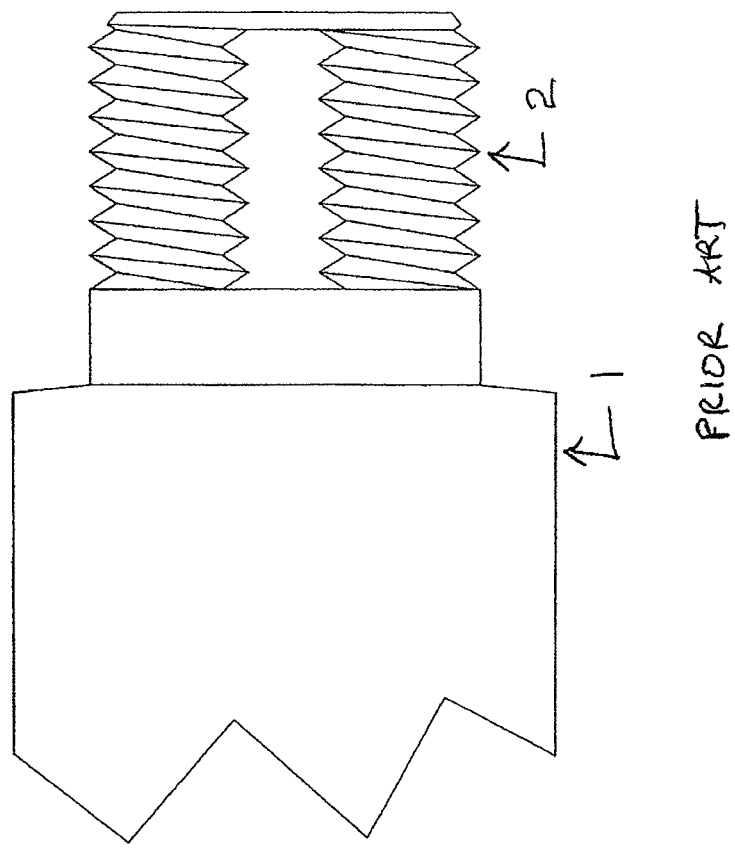
FIG. 1 shows an enlarged partial side view of a proximal end of a prior art pen needle or pre-loaded syringe/injection device. The proximal end is shown with the cap removed and in a prior-use state, i.e., it is ready to receive thereon a needle tip.
Figure 2:
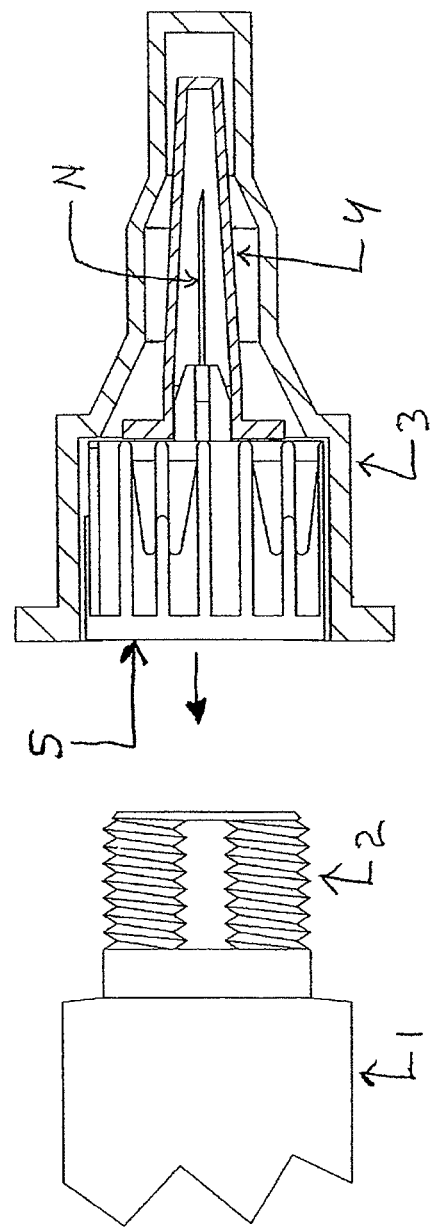
FIG. 2 shows the proximal end of FIG. 1 along with a prior art needle tip assembly in a position prior to installation onto the proximal end. The needle tip cap and the needle cap are both shown in cross-section.
Figure 3:
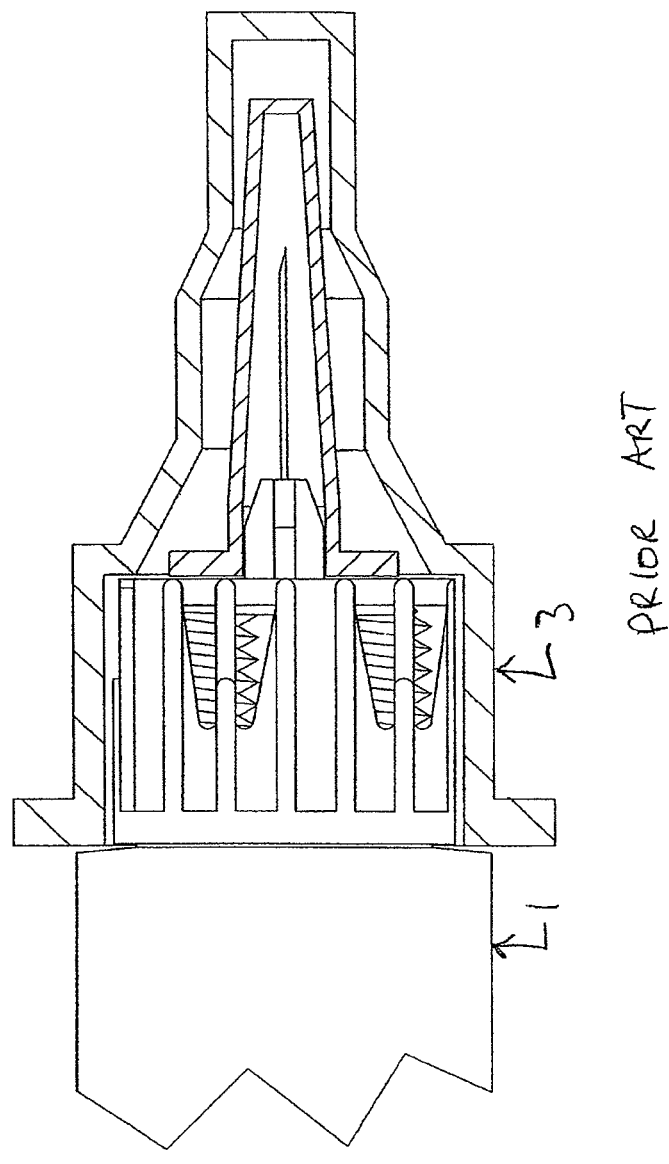
FIG. 3 shows the proximal end and prior art needle tip assembly of FIG. 2 after installation of the needle tip assembly onto the proximal end.
Figure 6:
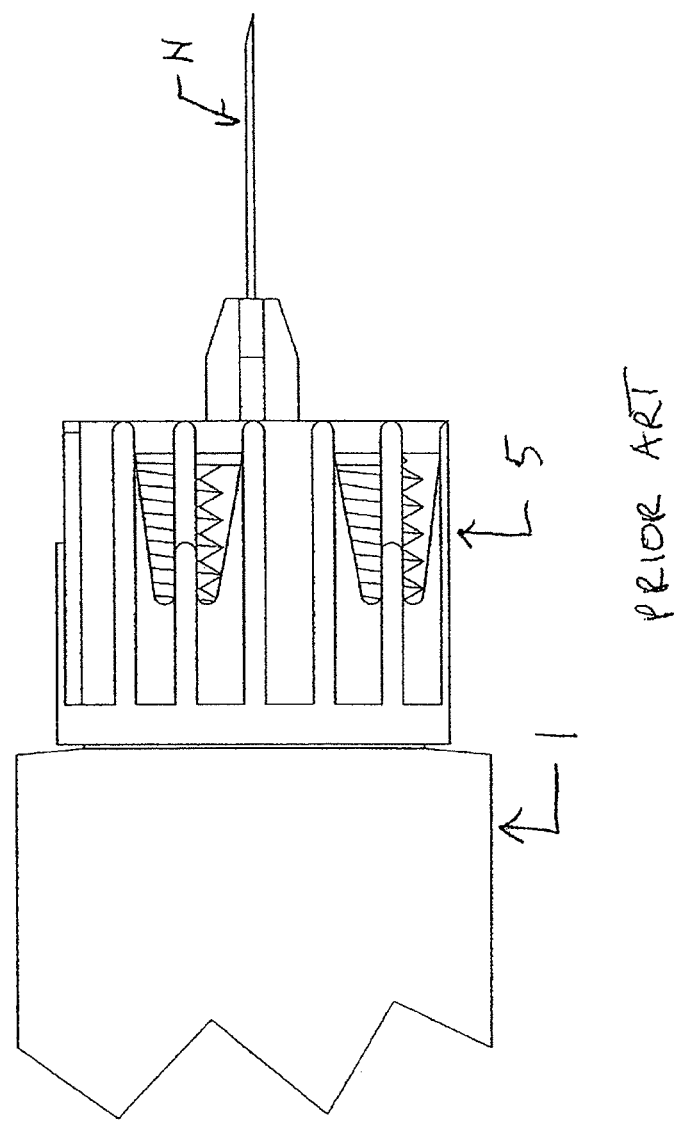
FIG. 6 shows the needle tip mounted onto the pen needle device in a position ready for injection according to the prior art.
Figure 7:
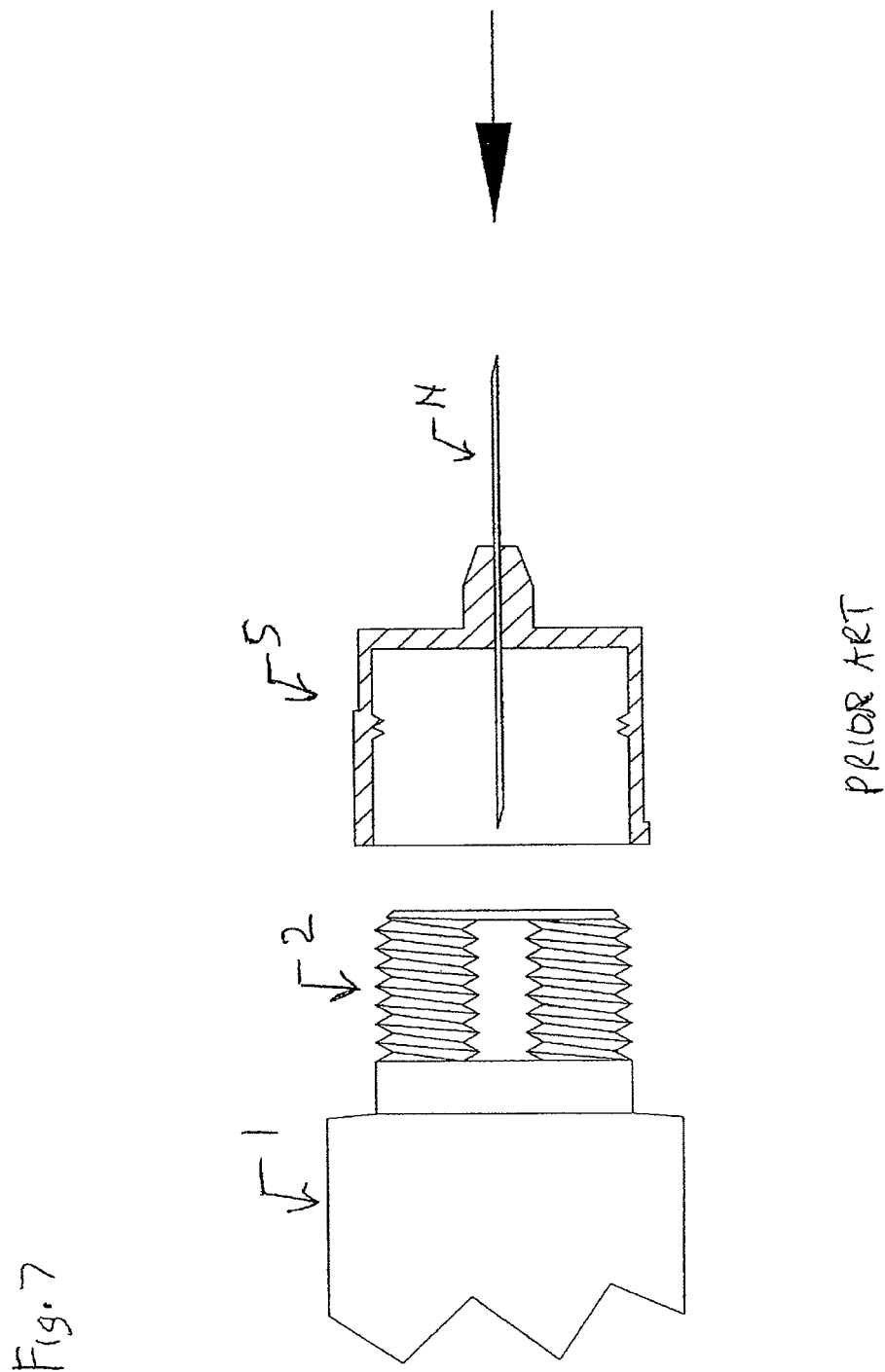
FIG. 7 shows the needle tip being removed from the pen needle device according to the prior art. This would occur after use and can occur by unthreading the needle tip from the threaded proximal end of the pen needle device. The arrow illustrates that it is possible to re-install the needle tip onto the threaded proximal end of the pen needle device.
Figure 8:
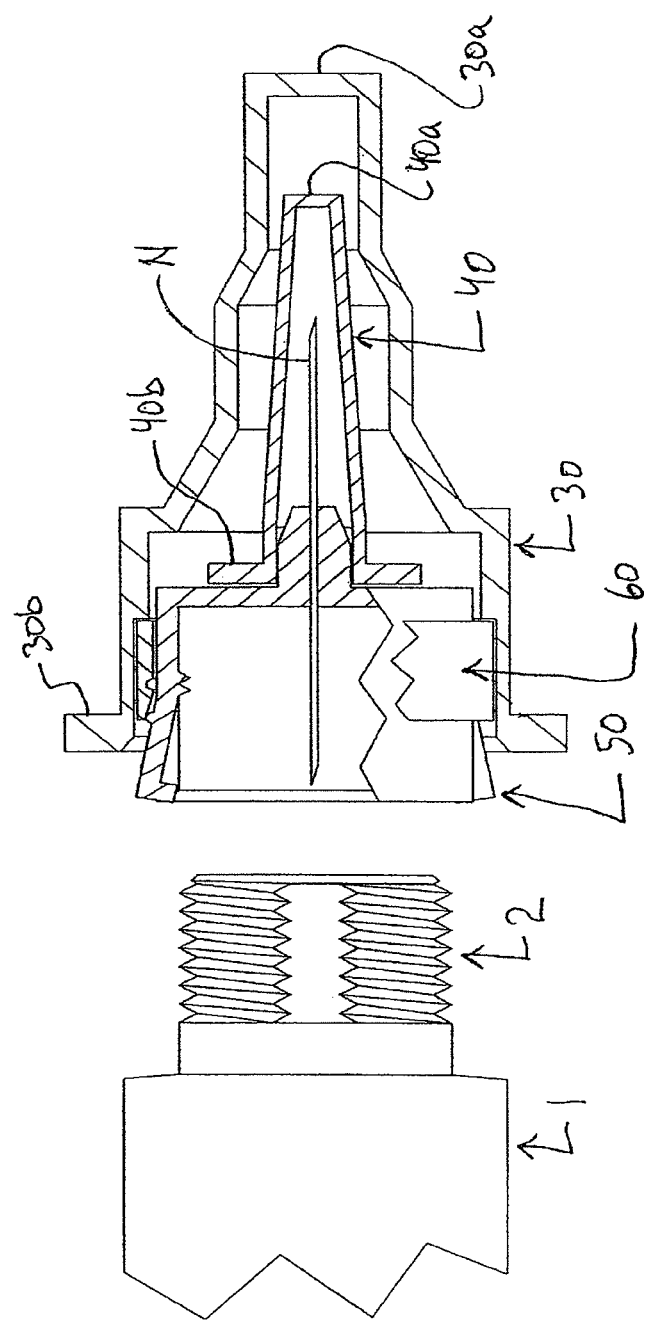
FIG. 8 shows the proximal end of FIG. 1 along with a needle tip assembly according to one embodiment of the invention. The needle tip assembly is shown in a position prior to installation onto the proximal end. The needle tip is shown in partial cross-section while the needle tip cap and the needle cap are shown in cross-section.

Referring now to the drawings and first to FIGS. 8-19 which shows a first embodiment of a needle tip assembly. The needle tip assembly includes a needle tip cap 30 having various generally cylindrical portions with different diameters, a needle cap 40, and a needle tip 50. The proximal end 30a of the needle tip cap 30 is closed while the distal end includes a circumferential flange 30b. The proximal end 40a of the needle cap 40 is closed while the distal end includes a circumferential flange 40b. The proximal end of the needle tip 50 includes a needle N while the distal end includes an opening which is sized to allow the needle tip 50 to be mounted to the threaded proximal end 2 of the pen needle device 1. In order to ensure that the needle tip 50 is prevented from being re-installed onto the proximal end 2, the needle tip 50 utilizes a ring 60 which can move axially from an initial position (see FIG. 9) to a second position (see FIG. 10) which causes one or more inwardly deflecting members 50a and 50b to deflect inwards by an amount which is sufficient to prevent the needle tip 50 (after being removed) from being re-installed onto the proximal end 2. As can be seen in FIG. 8, prior the needle tip assembly being installed onto the threaded proximal end 2, the one or more inwardly deflecting members 50a and 50b are bent outwardly or deflected outwardly by an amount which is sufficient to allow the needle tip 50 to be installed onto the proximal end 2 in the conventional manner, i.e., by axially sliding it on or by threading it on.

Figure 9:
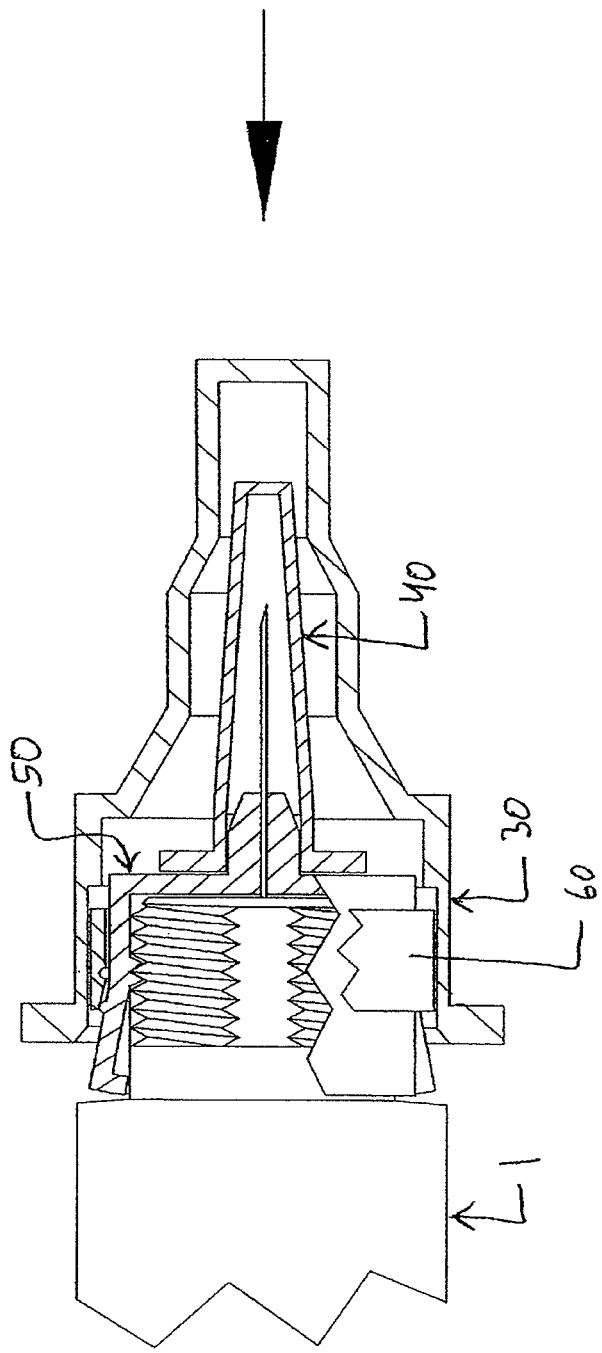
FIG. 9 shows the needle tip assembly of FIG. 8 after installation onto the proximal end.

As can be seen in FIG. 9, the needle tip assembly can be installed onto the threaded proximal end 2 without activating the re-use prevention mechanism, i.e., without causing the ring 60 to move axially to the locked position. Accordingly, in the position shown in FIG. 9, the one or more inwardly deflecting members 50a and 50b are still bent outwardly or deflected outwardly by an amount which is sufficient to allow the needle tip 50 to be installed onto the proximal end 2 in the conventional manner. Furthermore, while the ring 60 is in the position shown in FIG. 9, the needle tip assembly can be removed in the conventional way by, e.g., unthreading it off of the threaded end 2.

Figure 10:
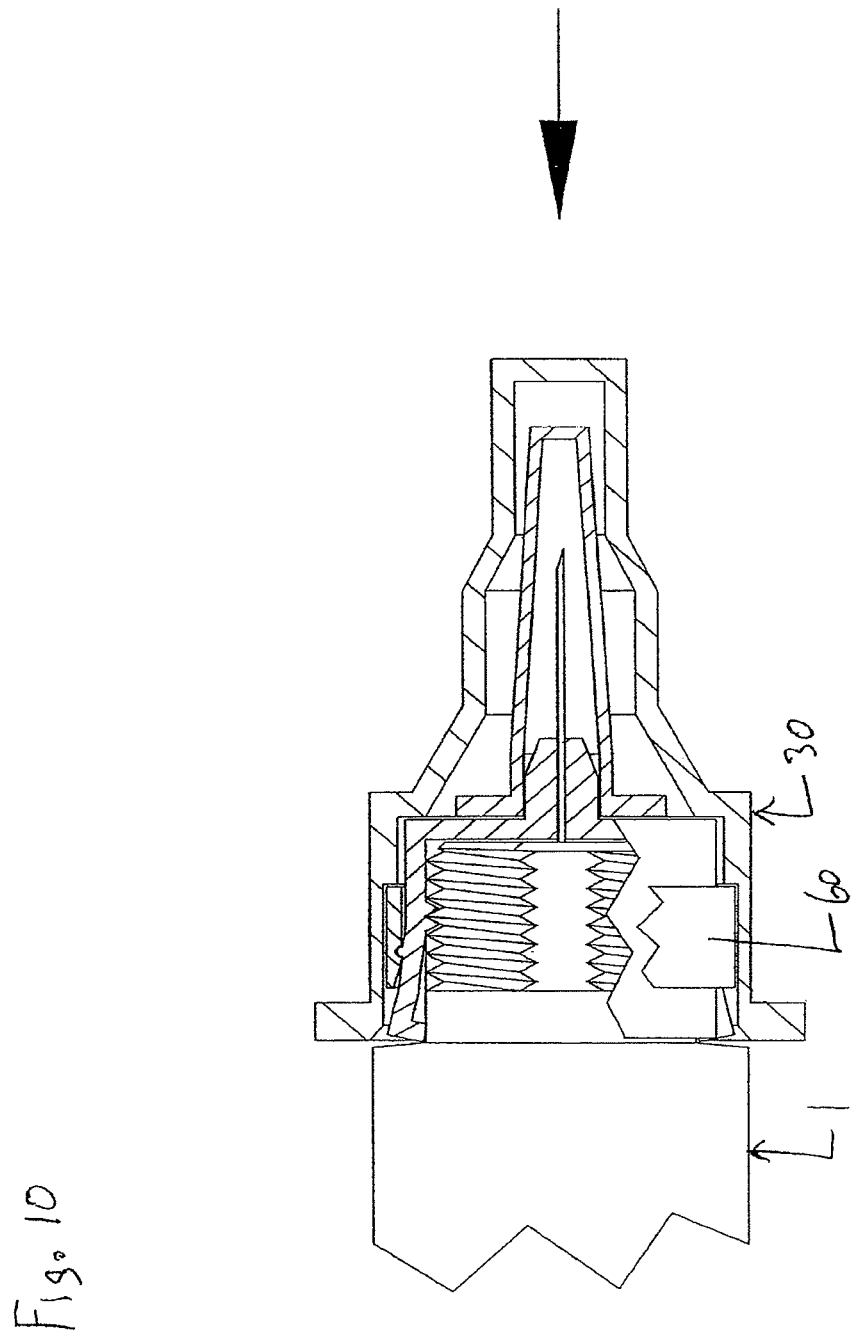
FIG. 10 shows the needle tip assembly of FIG. 9 after the needle tip cap is moved axially to a position which causes a ring to move to a locked position.

As can be seen in FIG. 10, after the needle tip assembly is installed onto the threaded proximal end 2 (as shown in FIG. 9), the needle tip cap 30 can be further moved axially in the distal direction (as indicated by the arrow in FIG. 10) to the point that it activates the re-use prevention system or mechanism, i.e., it causes the ring 60 to move axially in the distal direction until it assumes the locked position. The locked position is characterized by engagement between the projections of the one or more inwardly deflecting members 50a and 50b and the inner circumferential recess of the ring 60. Accordingly, in the position shown in FIG. 10, the one or more inwardly deflecting members 50a and 50b have been deflected inwardly so that they are now biased against the proximal end 2 and frictionally engage the threads thereof when the needle tip 50 is unthreaded. Furthermore, while the ring 60 is in the position shown in FIG. 10, the needle tip assembly can be removed, e.g., in the conventional way by unthreading it off of the threaded end 2, but, unlike the prior art, cannot thereafter be reinstalled.

Figure 13:
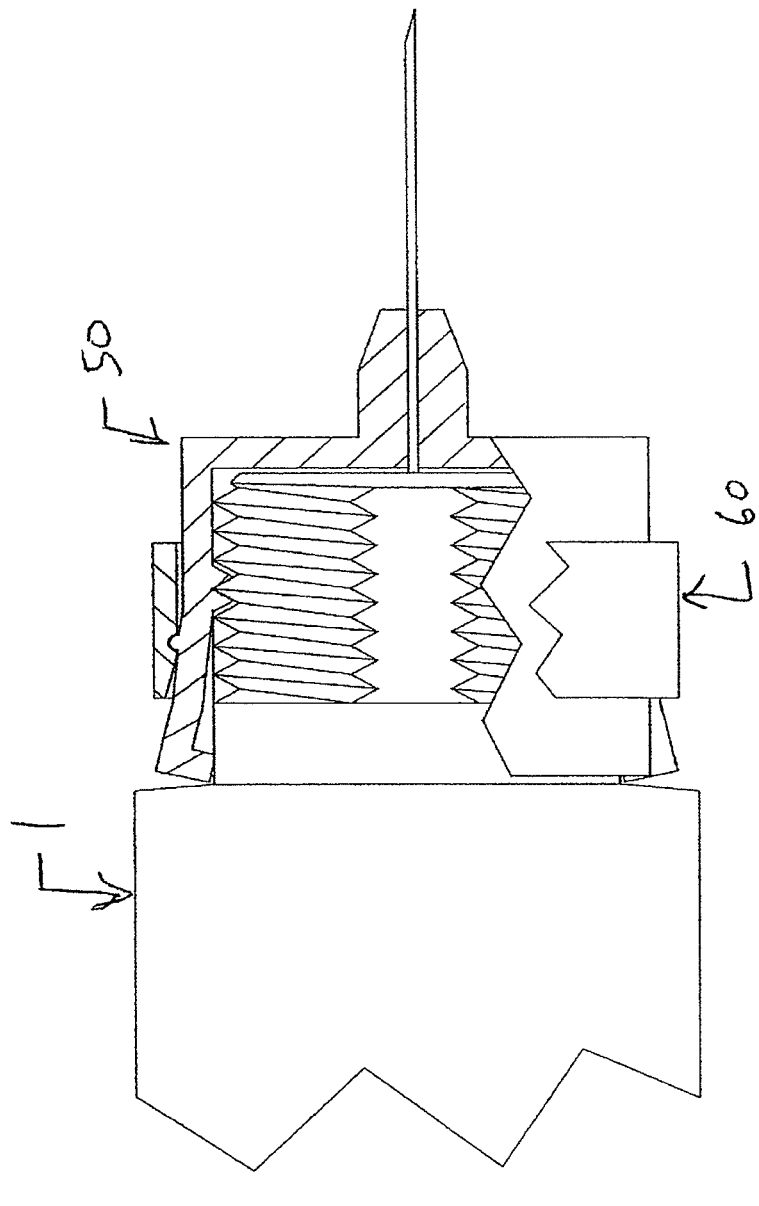
FIG. 13 shows the pen needle device with the installed needle tip of FIG. 12 in a position that is ready for injection. In this position, the ring has been moved to the locked position which has caused a plurality of inwardly deflecting members to engage the threaded proximal end of the pen needle device.

As can be seen in FIG. 11, once the needle tip assembly is installed (FIG. 9) and the re-use prevention system activated (FIG. 10), the needle tip cap 30 can be removed by sliding it off axially. Then, as shown in FIG. 12, the needle cap 40 can be removed. FIG. 13 shows the pen needle device with the installed needle tip 50 in a position that is ready for injection. Again, in this position, the ring 60 has been moved to the locked position which has caused a plurality of inwardly deflecting members 50a and 50b to frictionally engage the threaded proximal end 2 of the pen needle device 1.

Figure 14:
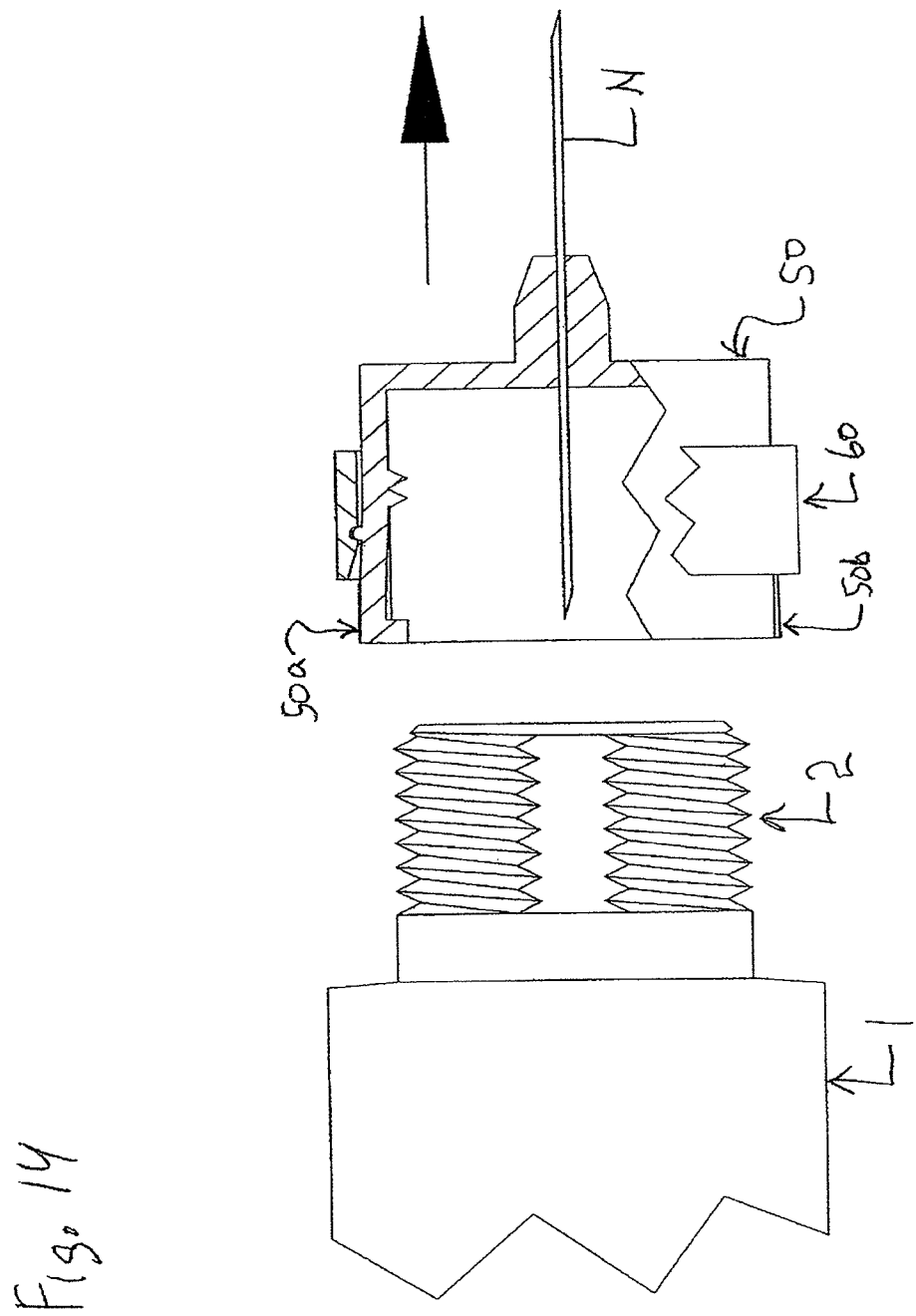
FIG. 14 shows the needle tip and proximal end of FIG. 13 after or as the needle tip is removed from the proximal end. As is evident from FIG. 14, because the ring has been moved to the locked position and caused a plurality of inwardly deflecting members to engage the threaded proximal end of the pen needle device, when the needle tip is removed, these inwardly deflecting members move inwardly to the point wherein they will interfere with and/or prevent re-installation of the needle tip.
Figure 15:
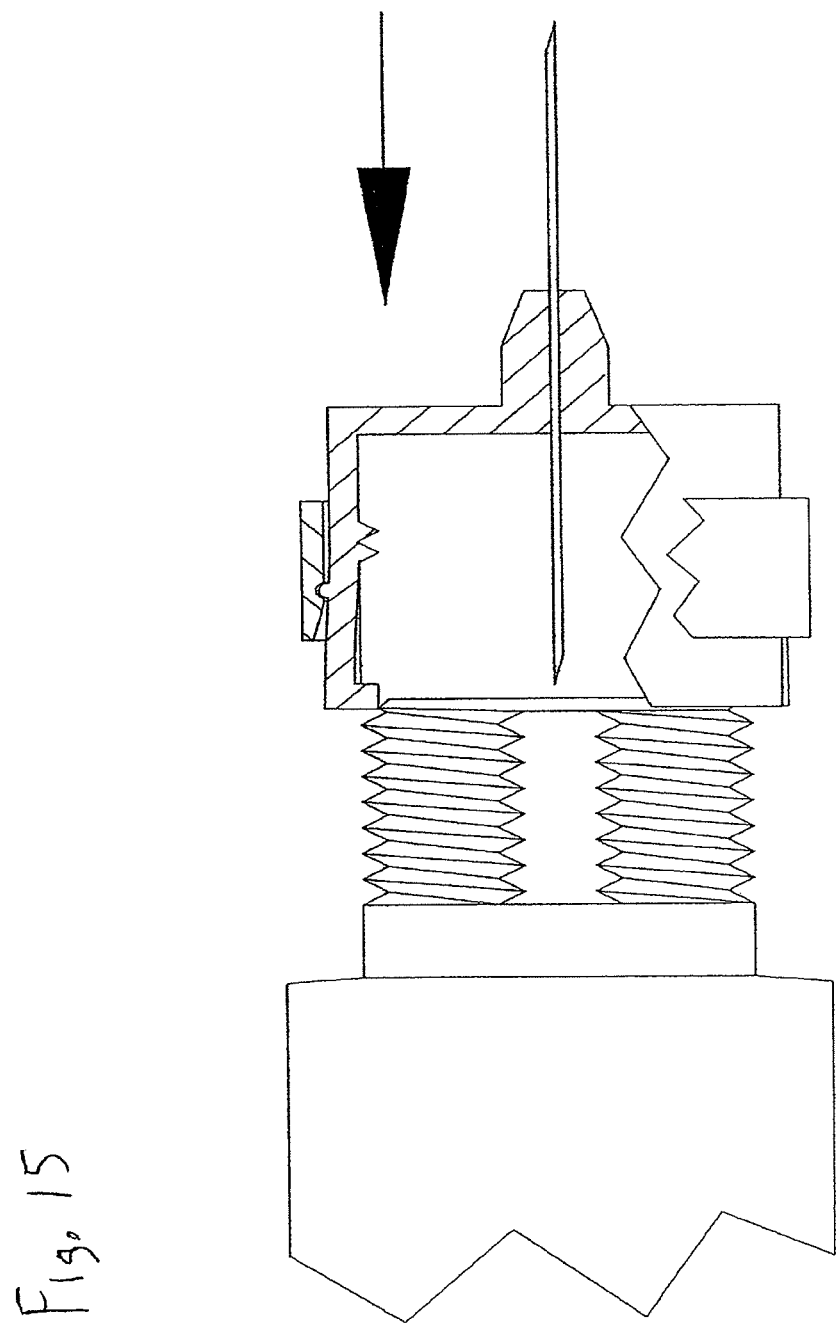
FIG. 15 shows how the inwardly deflecting members interfere with and/or prevent re-installation of the needle tip, i.e., the inwardly oriented projections do not threadably engage with the threads of the proximal end and function to, in effect, reduce a diameter of the distal opening of the needle tip to the point that it is smaller than the outer diameter of the proximal end.

As can be seen in FIG. 14, once the pen needle device with the installed needle tip assembly has been used to perform an injection, the needle tip 50 can be removed in the following ways: one could simply grip the needle tip 50 in the area of the ring 60 and unthread it from the threaded proximal end 2. This is risky, of course, because the user can be inadvertently be pricked by the exposed needle N; one could re-install the needle cap 40 and then grip the needle tip 50 in the area of the ring 60 and unthread it from the threaded proximal end 2; one could re-install both the needle cap 40 and the needle tip cap 30, and then grip the needle tip cap 30 in the area just in front of the flange 30b and thereafter unthread the entire needle tip assembly thereby causing the needle tip 50 to become unthreaded from the threaded proximal end 2; and one could re-install only the needle tip cap 30, and then grip the needle tip cap 30 in the area just in front of the flange 30b and thereafter unthread the needle tip assembly (without the cap 40) thereby causing the needle tip 50 to become unthreaded from the threaded proximal end 2. All of these ways are contemplated by the invention, but the first way is the least desirable.

As is evident from FIG. 14, once the needle tip 50 is removed from the threaded proximal end 2 (and because the ring 60 has been moved to the locked position), the plurality of inwardly deflecting members 50a and 50b are caused to move inwardly to the point that they will not permit (i.e., they will interfere with) re-installation of the needle tip 50 back onto the threaded proximal end 2 of the pen needle device 1. This is evident from FIG. 15 which shows how the plurality of inwardly deflecting members 50a and 50b have been moved inwardly to the point that they will not permit (i.e., they will interfere with) re-installation of the needle tip 50 back onto the threaded proximal end 2 of the pen needle device 1 owing to the fact that they effectively reduce the diameter of the distal opening of the needle tip 50.

Figure 17:
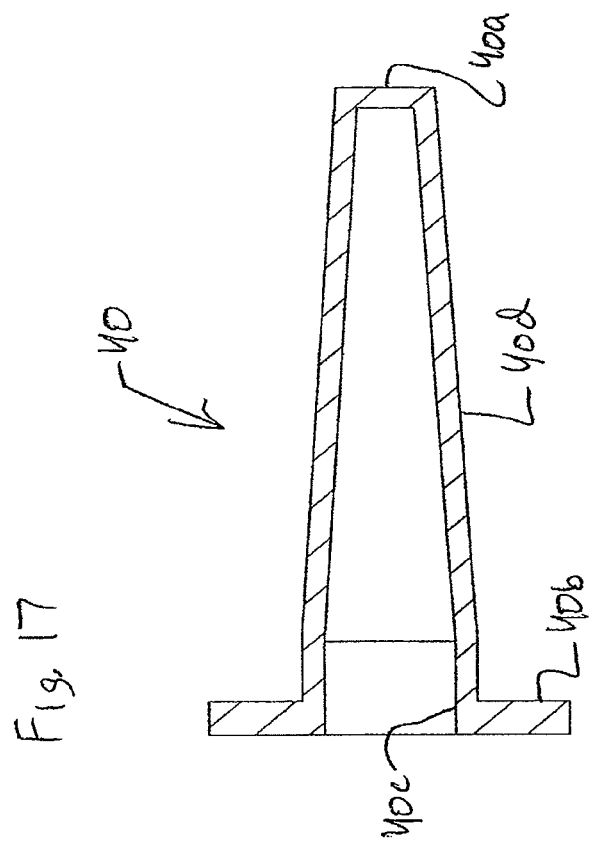
FIG. 17 shows a side cross-section view of the needle cap of FIG. 16.
Figure 16:
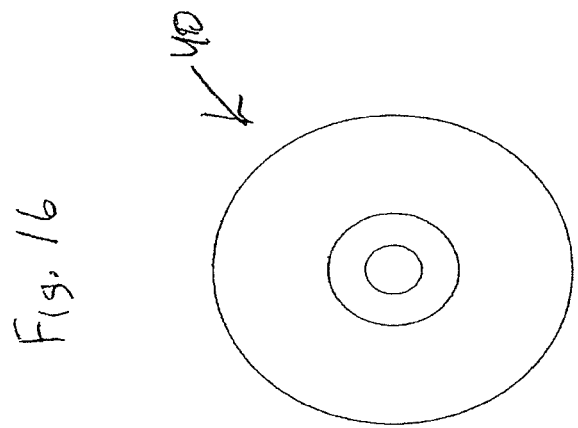
FIG. 16 shows a distal end view of the needle cap which can be used in the needle tip assembly according to the invention.

As is evident from FIGS. 16 and 17, the needle cap 40 has a closed proximal end 40a, an open distal end having a circumferential flange 40b, a distal opening 40c sized to frictionally engage with a hub portion of the needle tip 50, and a tapered portion 40d which is sized to safely receive therein the needle N. Of course, the needle cap 40 can have any desired configuration provided that it functions for its intended purpose, and can even be dispensed with without leaving the scope of the invention.

As is evident from FIGS. 18 and 19, the needle tip cap 30 has a closed proximal end 30a, an open distal end having a circumferential flange 30b, a distal opening 30c sized to receive therein the ring 60, a shoulder 30c which engages with a distal end of the ring 60 so as to cause the ring 60 to move to the locked position, a generally circumferential surface 30e which is sized to frictionally engage with an outer surface of the needle tip 50 so as to cause it to rotate relative to the proximal end 2, and a tapered and/or stepped portion 30f which is sized to safely receive therein the needle N and the needle cap 40. Of course, the needle tip cap 30 can have any desired configuration provided that it functions for its intended purpose, and can even be dispensed with without leaving the scope of the invention. In the later case, only the needle cap 40 (or even one of the type shown in FIGS. 53 and 54) would need to be utilized (for safety reasons) and the user could activate the re-use prevention system by gripping the ring 60 and sliding it distally until it assumes the locked position.

Figure 20:
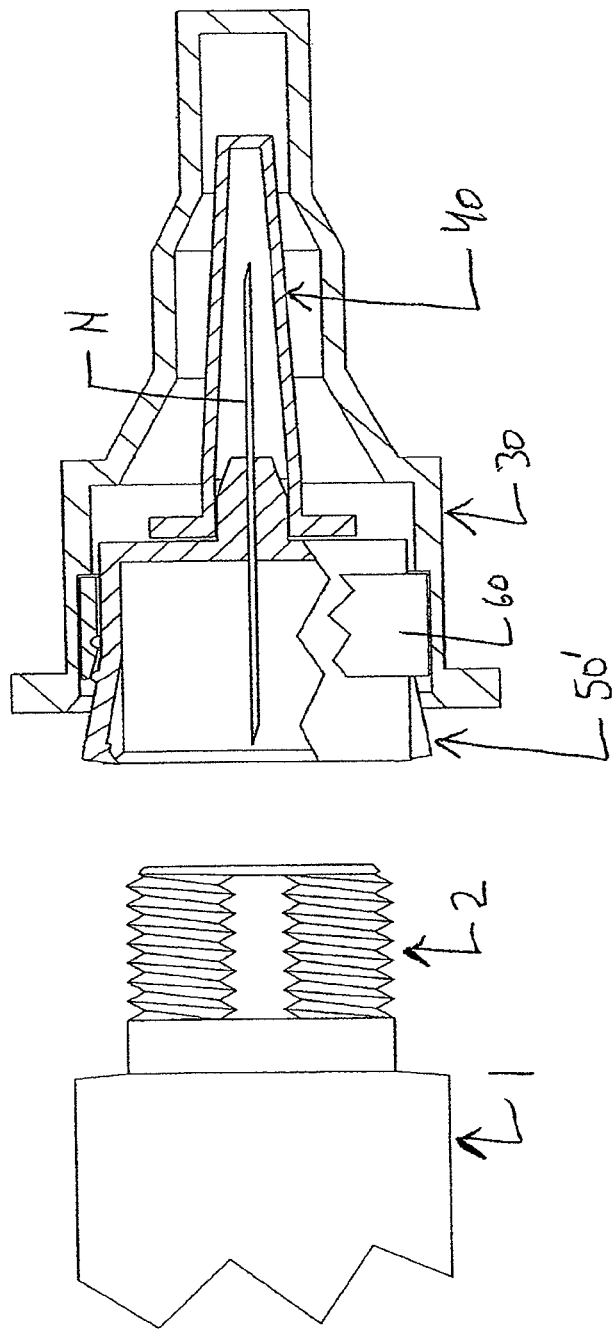
FIG. 20 shows the proximal end of FIG. 1 along with a needle tip assembly according to another embodiment of the invention. The needle tip assembly is shown in a position prior to installation onto the proximal end. The needle tip is shown in partial cross-section while the needle tip cap and the needle cap are shown in cross-section.

FIGS. 20-28 shows a second embodiment of a needle tip assembly. The needle tip assembly includes a needle tip cap 30 having various generally cylindrical portions with different diameters, a needle cap 40, and a needle tip 50'. As the needle tip cap 30, the needle cap 40, and the ring 60 of the instant embodiment are essentially identical to those used in the previous embodiment, they have been accorded the same reference numerals. The proximal end 30a of the needle tip cap 30 is closed while the distal end includes a circumferential flange 30b. Similarly, the proximal end 40a of the needle cap 40 is closed while the distal end includes a circumferential flange 40b. The proximal end of the needle tip 50' includes a needle N while the distal end includes an opening which is sized to allow the needle tip 50' to be mounted to the threaded proximal end 2 of the pen needle device 1. In order to ensure that the needle tip 50' is prevented from being re-installed onto the proximal end 2, the needle tip 50' utilizes a ring 60 which can move axially from an initial position (see FIG. 21) to a second position (see FIG. 22) which causes one or more inwardly deflecting members 50'a and 50'b to deflect inwards by an amount which is sufficient to prevent the needle tip 50' (after being removed) from being re-installed onto the proximal end 2. As can be seen in FIG. 20, prior the needle tip assembly being installed onto the threaded proximal end 2, the one or more inwardly deflecting members 50'a and 50'b are bent outwardly or deflected outwardly by an amount which is sufficient to allow the needle tip 50' to be installed onto the proximal end 2 in the conventional manner, i.e., by axially sliding it on or by threading it on.

As can be seen in FIG. 21, the needle tip assembly can be installed onto the threaded proximal end 2 without activating the re-use prevention system or mechanism, i.e., without causing the ring 60 to move axially to the locked position. Accordingly, in the position shown in FIG. 21, the one or more inwardly deflecting members 50'a and 50'b are still bent outwardly or deflected outwardly by an amount which is sufficient to allow the needle tip 50' to be installed onto the proximal end 2. Furthermore, while the ring 60 is in the position shown in FIG. 21, the needle tip assembly can be removed in the conventional way, e.g., by unthreading it off of the threaded end 2.

As can be seen in FIG. 22, after the needle tip assembly is installed onto the threaded proximal end 2 (as shown in FIG. 21), the needle tip cap 30 can be further moved axially in the distal direction (as indicated by the arrow in FIG. 22) to the point that it activates the re-use prevention system or mechanism, i.e., it causes the ring 60 to move axially in the distal direction until it assumes the locked position. The locked position is characterized by engagement between the projections of the one or more inwardly deflecting members 50' and 50' and the inner circumferential recess of the ring 60. Accordingly, in the position shown in FIG. 22, the one or more inwardly deflecting members 50'a and 50'b have been deflected inwardly so that they are now biased against the proximal end 2 and frictionally engage the threads thereof when the needle tip 50' is unthreaded. Furthermore, while the ring 60 is in the position shown in FIG. 22, the needle tip assembly can be removed, e.g., in the conventional way by unthreading it off of the threaded end 2, but, unlike the prior art, cannot thereafter be reinstalled.

Figure 25:
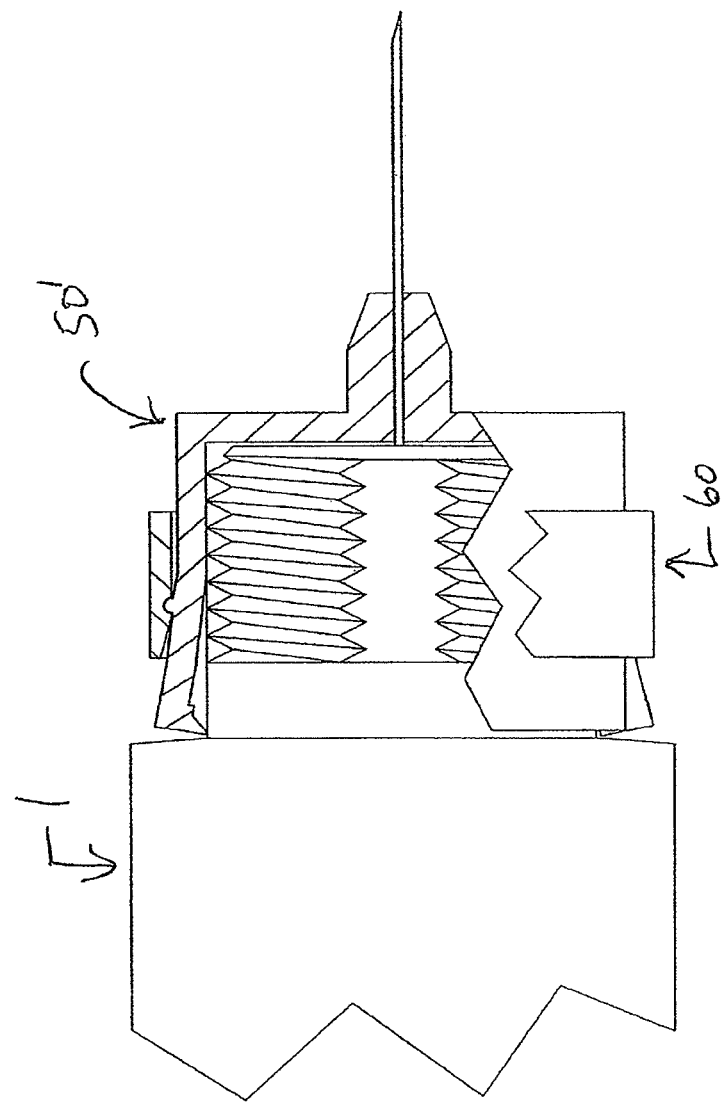
FIG. 25 shows the pen needle device with the installed needle tip of FIG. 24 in a position that is ready for injection. In this position, the ring has been moved to the locked position which has caused a plurality of inwardly deflecting members to engage the threaded proximal end of the pen needle device.

As can be seen in FIG. 23, once the needle tip assembly is installed (FIG. 21) and the re-use prevention system activated (FIG. 22), the needle tip cap 30 can be removed by sliding it off axially. Then, as shown in FIG. 24, the needle cap 40 can also be removed axially. FIG. 25 shows the pen needle device with the installed needle tip 50' in a position that is ready for injection. Again, in this position, the ring 60 has been moved to the locked position which has caused a plurality of inwardly deflecting members 50'a and 50'b to frictionally engage the threaded proximal end 2 of the pen needle device 1.

Figure 26:
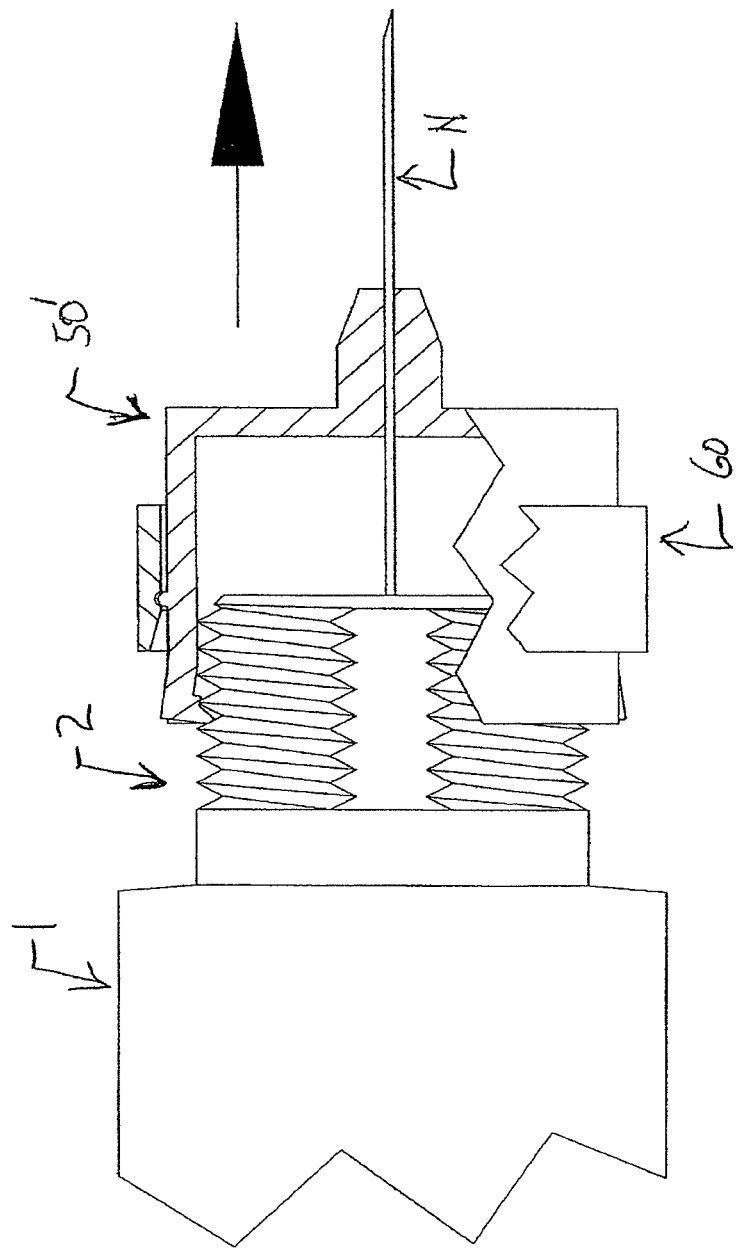
FIG. 26 shows the needle tip and proximal end of FIG. 25 as the needle tip is removed from the proximal end. Unlike the previous embodiment which utilizes internal threads arranged within the needle tip to threadably engage with the treads of the proximal end of the pen needle device, this embodiment relies upon a threaded engagement between the inwardly projecting members and the threaded proximal end of the pen needle device for removal of the needle tip. As is evident from FIG. 26, because the ring has been moved to the locked position and caused a plurality of inwardly deflecting members to engage the threaded proximal end of the pen needle device, when the needle tip is removed, these inwardly deflecting members move inwardly to the point wherein they will interfere with and/or prevent re-installation of the needle tip.

As can be seen in FIGS. 26 and 27, once the pen needle device with the installed needle tip assembly has been used to perform an injection, the needle tip 50' can be removed in the following ways: one could simply grip the needle tip 50' in the area of the ring 60 and unthread it from the threaded proximal end 2. This is risky, of course, because the user can be inadvertently be pricked by the exposed needle N; one could re-install the needle cap 40 and then grip the needle tip 50' in the area of the ring 60 and unthread it from the threaded proximal end 2; one could re-install both the needle cap 40 and the needle tip cap 30, and then grip the needle tip cap 30 in the area just in front of the flange 30b and thereafter unthread the entire needle tip assembly thereby causing the needle tip 50' to become unthreaded from the threaded proximal end 2; and one could re-install only the needle tip cap 30, and then grip the needle tip cap 30 in the area just in front of the flange 30b and thereafter unthread the needle tip assembly (without the cap 40) thereby causing the needle tip 50' to become unthreaded from the threaded proximal end 2. As was the case in the previous embodiment, all of these ways are contemplated by the invention for this embodiment, with, however, the first way being the least desirable.

As is evident from FIG. 28, once the needle tip 50' is removed from the threaded proximal end 2 (and because the ring 60 has been moved to the locked position), the plurality of inwardly deflecting members 50'a and 50'b are caused to move inwardly to the point that they will not permit (i.e., they will interfere with) re-installation of the needle tip 50' back onto the threaded proximal end 2 of the pen needle device 1. This is evident from FIG. 28 which shows how the plurality of inwardly deflecting members 50'a and 50'b have been moved inwardly to the point that they will not permit (i.e., they will interfere with) re-installation of the needle tip 50' back onto the threaded proximal end 2 of the pen needle device 1 owing to the fact that they effectively reduce the diameter of the distal opening of the needle tip 50'. As is evident from comparing FIGS. 28 and 15, the needle tip 50' differs from the needle tip 50 in that it does not utilize any internal threads in the body of the needle tip 50' (i.e., the distal opening which receives therein the threaded proximal end 2 is generally cylindrical and smooth) and with regard to the shape of the projections which extend inwardly from the members 50a/50'a and 50b/50'b. That is, the projections which extend inwardly from the members 50a and 50b have a generally blunt end or rectangular-shaped cross-section whereas the projections which extend inwardly from the members 50'a and 50'b have a generally tapered end or triangular-shaped cross-section so as to threadably engage with the threads of the proximal end 2.

Figure 48:
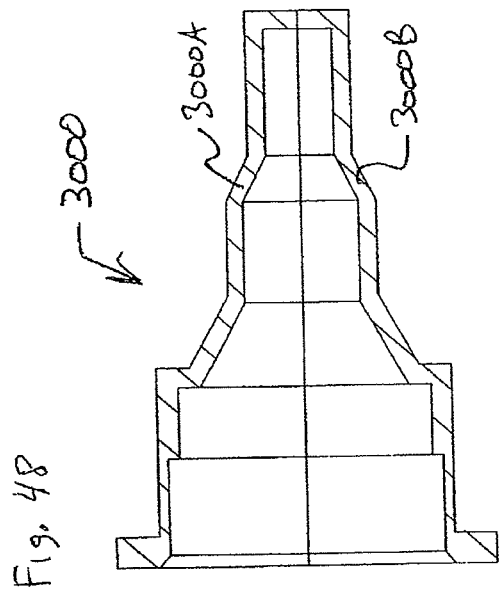
FIG. 48 shows a side cross-section view of the needle tip cap shown in FIG. 47.
Figure 47:
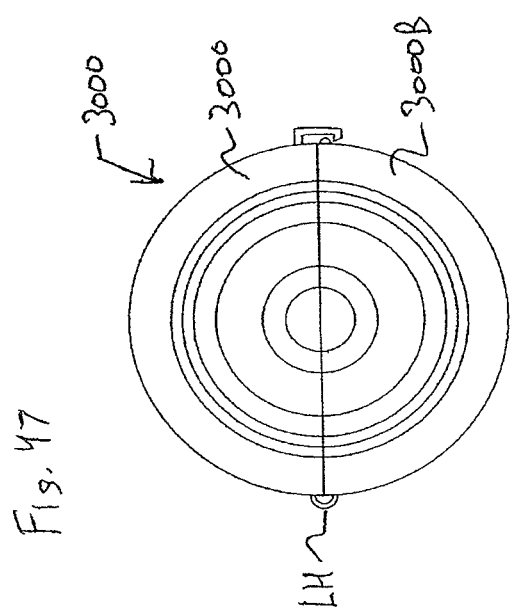
FIG. 47 shows a distal end view of another embodiment of a needle tip cap which can be used with one or more of the needle tip assembly embodiments. The needle tip cap is of a two-piece construction which pieces are connected one side with a living hinge and on the other side with a snap-together lock system.
Figure 49:
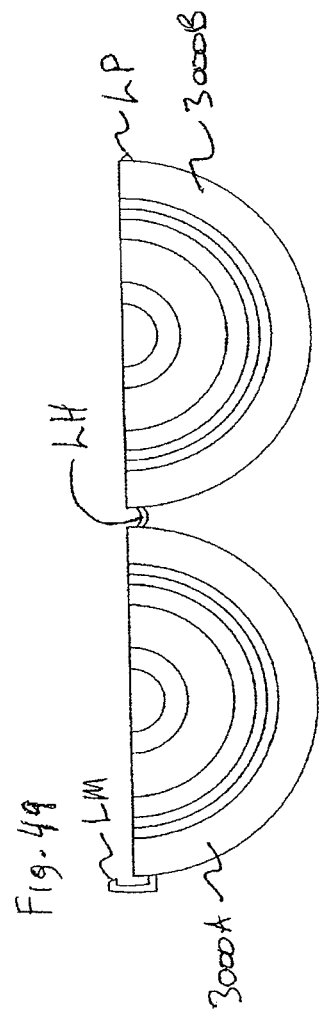
FIG. 49 shows another distal end view of the needle tip cap shown in FIG. 47 except that the two-piece construction is shown in the open position.

Although not shown, the embodiment shown in FIGS. 20-28 can instead, like the previous embodiment, utilize the needle tip cap shown in FIGS. 47-49. Of course, the needle tip cap 30 can have any desired configuration provided that it functions for its intended purpose, and can even be dispensed with without leaving the scope of the invention. In the later case, only the needle cap 40 (or even one of the type shown in FIGS. 53 and 54) would need to be utilized (for safety reasons) and the user could activate the re-use prevention system by gripping the ring 60 and sliding it distally until it assumes the locked position.

FIGS. 29 and 30 show an optional needle tip 50" which can be used with any of the embodiments disclosed herein. For purposes of clarity, the ring 60 has been removed. Unlike the previous embodiments which utilize two oppositely arranged inwardly deflecting members 50a/50'a and 50b/50'b which are caused to move inwardly by the ring 60, this embodiment utilizes four equally angularly spaced members 50"a, 50"b, 50"c and 50"d, which can be moved inwardly by the ring 60 to the point that they will not permit (i.e., they will interfere with) re-installation of the needle tip 50" back onto the threaded proximal end 2 of the pen needle device 1 owing to the fact that they effectively reduce the diameter of the distal opening of the needle tip 50".

Although the members 50"a, 50"b, 50"c and 50"d are shown deflected inwardly (for purposes of clarity), of course this would not occur until the ring 60 has been moved to the locked position. The needle tip 50", like the second embodiment, does not utilize any internal threads in the body of the needle tip 50" (i.e., the distal opening which receives therein the threaded proximal end 2 is generally cylindrical and smooth) and utilizes projections P which extend inwardly from the members 50"a, 50"b, 50"c and 50"d and have a generally tapered end or triangular-shaped cross-section so as to threadably engage with the threads of the proximal end 2. The projections P can extend all the way across the width of each of the members 50"a, 50"b, 50"c and 50"d (as shown in FIG. 29) or they have other forms such as ones which are shorter than the width of the members 50"a, 50"b, 50"c and 50"d. The projections P may even have the form of centrally disposed circular or rounded projections. Other configurations may also be utilized provided they are capable of locking with an/or frictionally engaging with the ring 60.

Figure 32:
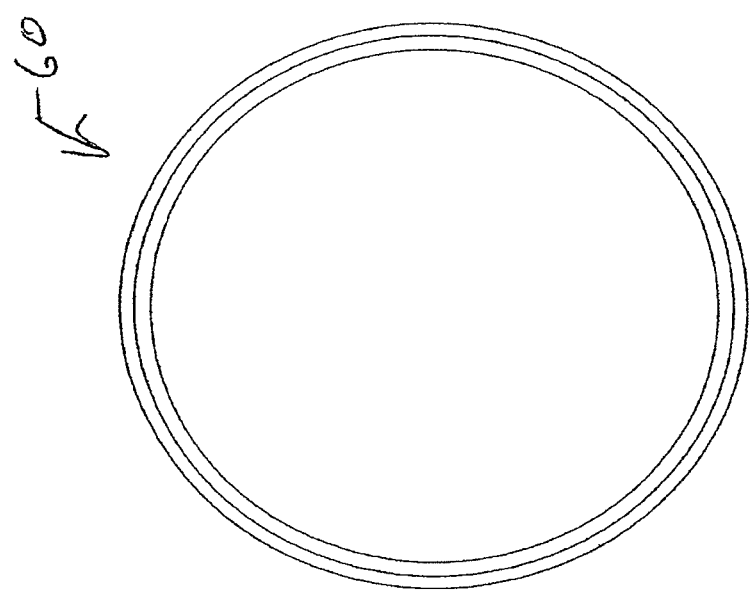
FIG. 32 shows a distal end view of the ring of FIG. 31.
Figure 31:
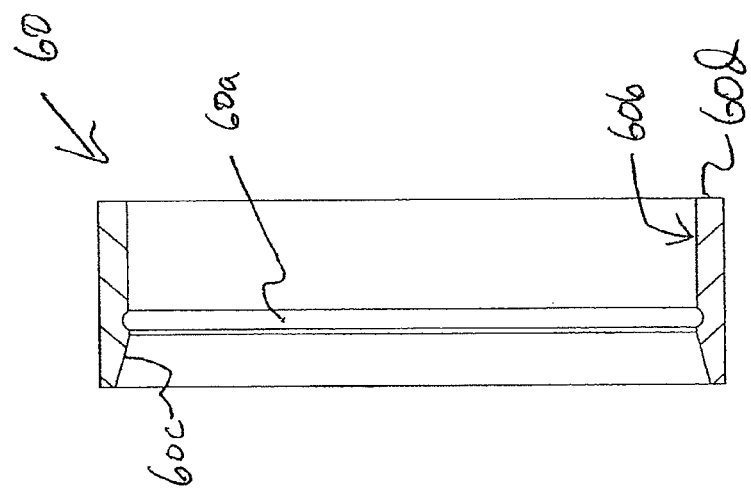
FIG. 31 shows a cross-section view of the ring which can be used in the embodiments shown in FIGS. 8-30.

As is evident from FIGS. 31 and 32, the ring 60 which can be used in the previous embodiments is generally cylindrical and has a proximal end 60d which engages the shoulder 30c of the needle tip cap 30, a distal end having a tapered inner surface 60c configured to facilitate sliding over the deflecting members 50a/50b or 50'a/50'b or 50"a/50"b/50"c/50"d, a circumferential recess 60a sized and configured to receive therein the projections P of the members 50a/50b or 50'a/50'b or 50"a/50"b/50"c/50"d, and an inner cylindrical surface 60b which is sized to slide over the needle tip body. Of course, the ring 60 can have any desired configuration provided that it functions for its intended purpose.

FIG. 33 shows still another embodiment of a needle tip assembly. The needle tip assembly includes a needle tip cap 30 having various generally cylindrical portions with different diameters, a needle cap 40, and a needle tip 50$^{III}$. As the needle tip cap 30 and the needle cap 40 of the instant embodiment are essentially identical to those used in the previous embodiment, they have been accorded the same reference numerals. In this embodiment also, the proximal end 30a of the needle tip cap 30 is closed while the distal end includes a circumferential flange 30b. Similarly, the proximal end 40a of the needle cap 40 is closed while the distal end includes a circumferential flange 40b. The proximal end of the needle tip 50$^{III}$ includes a needle N while the distal end includes an opening which is sized to allow the needle tip 50$^{III}$ to be mounted to the threaded proximal end 2 of the pen needle device 1. In order to ensure that the needle tip 50$^{III}$ is prevented from being re-installed onto the proximal end 2, the needle tip 50$^{III}$ utilizes a ring 60' which can move axially from an initial position (similar to the position shown in FIG. 21) to a second position (similar to the position shown in FIG. 22) which causes the four inwardly deflecting members 50$^{III}$a, 50$^{III}$b, 50$^{III}$c and 50$^{III}$d to deflect inwards by an amount which is sufficient to prevent the needle tip 50$^{III}$ (after being removed) from being re-installed onto the proximal end 2. As can be seen in FIG. 33, prior to the needle tip assembly being installed onto the threaded proximal end 2 (not shown in FIG. 33), the four inwardly deflecting members 50$^{III}$a, 50$^{III}$b, 50$^{III}$c and 50$^{III}$d are bent outwardly or deflected outwardly by an amount which is sufficient to allow the needle tip 50$^{III}$ to be installed onto the proximal end 2 in the conventional manner, i.e., by axially sliding it on or by threading it on.

In a manner similar to that shown FIG. 21, the needle tip assembly of FIG. 33 can be installed onto the threaded proximal end 2 without activating the re-use prevention system or mechanism, i.e., without causing the ring 60' to move axially to the second or activated position. Accordingly, in the position shown in FIG. 33, the one or more inwardly deflecting members $50^{III}a$, $50^{III}b$, $50^{III}c$ and $50^{III}d$ are still bent outwardly or deflected outwardly by an amount which is sufficient to allow the needle tip $50^{III}$ to be installed onto the proximal end 2. Furthermore, while the ring 60' is in the position shown in FIG. 33, the needle tip assembly can be removed in the conventional way, e.g., by unthreading it off of the threaded end 2.

In the same way as was shown in FIG. 22, after the needle tip assembly shown in FIG. 33 is installed onto the threaded proximal end 2 (similar to that shown in FIG. 21), the needle tip cap 30 can be further moved axially in the distal direction (as indicated by the arrow in FIG. 22) to the point that it activates the re-use prevention system or mechanism, i.e., it causes the ring 60' to move axially in the distal direction until it assumes the second or activated position. Unlike the previous embodiments which provide for a locking position, i.e., characterized by engagement between the projections of the inwardly deflecting members and the inner circumferential recess of the ring, this embodiment utilizes no projections on the members $50^{III}a$, $50^{III}b$, $50^{III}c$ and $50^{III}d$ and does not therefore utilize the recess for receiving the same on the ring 60'. Instead, the ring 60' merely frictionally engages with the outer surfaces of the members $50^{III}a$, $50^{III}b$, $50^{III}c$ and $50^{III}d$ when it is moved to the second or activated position. In order to ensure that the ring 60' does not move back to the original position (after being moved to the second position), the inner circumferential surface of the ring 60' and the outer surface of the members $50^{III}a$, $50^{III}b$, $50^{III}c$ and $50^{III}d$ can be provided with high friction surfaces such as e.g., a knurl, a high friction coating, etc. Although not shown, when the ring 60' is moved to the second or activated position, the inwardly deflecting members $50^{III}a$, $50^{III}b$, $50^{III}c$ and $50^{III}d$ will be deflected inwardly (as was the case in the previous embodiments) so that they will biased against the proximal end 2 and frictionally engage the threads thereof when the needle tip $50^{III}$ is unthreaded.

As was the case in the previous embodiments, once the needle tip assembly shown in FIG. 33 is installed and the re-use prevention system activated, the needle tip cap 30 can be removed by sliding it off axially. Then, the needle cap 40 can also be removed axially. Once the pen needle device with the installed needle tip assembly has been used to perform an injection, the needle tip $50^{III}$ can be removed in the following ways: one could simply grip the needle tip $50^{III}$ in the area of the ring 60' and unthread it from the threaded proximal end 2. This is risky, of course, because the user can be inadvertently be pricked by the exposed needle N; one could re-install the needle cap 40 and then grip the needle tip $50^{III}$ in the area of the ring 60' and unthread it from the threaded proximal end 2; one could re-install both the needle cap 40 and the needle tip cap 30, and then grip the needle tip cap 30 in the area just in front of the flange 30b and thereafter unthread the entire needle tip assembly thereby causing the needle tip $50^{III}$ to become unthreaded from the threaded proximal end 2; and one could re-install only the needle tip cap 30, and then grip the needle tip cap 30 in the area just in front of the flange 30b and thereafter unthread the needle tip assembly (without the cap 40) thereby causing the needle tip $50^{III}$ to become unthreaded from the threaded proximal end 2. As was the case in the previous embodiments, all of these ways are contemplated by the invention for this embodiment, with, however, the first way being the least desirable.

As was the case in the embodiment shown in FIGS. 20-28, once the needle tip $50^{III}$ is removed from the threaded proximal end 2 (and because the ring 60' has been moved to the activated position), the plurality of inwardly deflecting members $50^{III}a$, $50^{III}b$, $50^{III}c$ and $50^{III}d$ are caused to move inwardly to the point that they will not permit (i.e., they will interfere with) re-installation of the needle tip $50^{III}$ back onto the threaded proximal end 2 of the pen needle device 1. This occurs in substantially the same way as was shown in FIG. 28 which shows how the plurality of inwardly deflecting members have been moved inwardly to the point that they will not permit (i.e., they will interfere with) re-installation of the needle tip $50^{III}$ back onto the threaded proximal end 2 of the pen needle device 1 owing to the fact that they effectively reduce the diameter of the distal opening of the needle tip $50^{III}$.

Although not shown, the embodiment shown in FIG. 33 can, like the previous embodiments, utilize the needle tip cap shown in FIGS. 47-49 instead of the needle tip cap 30 shown in FIG. 33. Of course, the needle tip cap 30 can also have any desired configuration provided that it functions for its intended purpose, and can even be dispensed with without leaving the scope of the invention. In the later case, only the needle cap 40 (or even one of the type shown in FIGS. 53 and 54) would need to be utilized (for safety reasons) and the user could activate the re-use prevention system by gripping the ring 60' and sliding it distally until it assumes the activated position.

Figure 34:
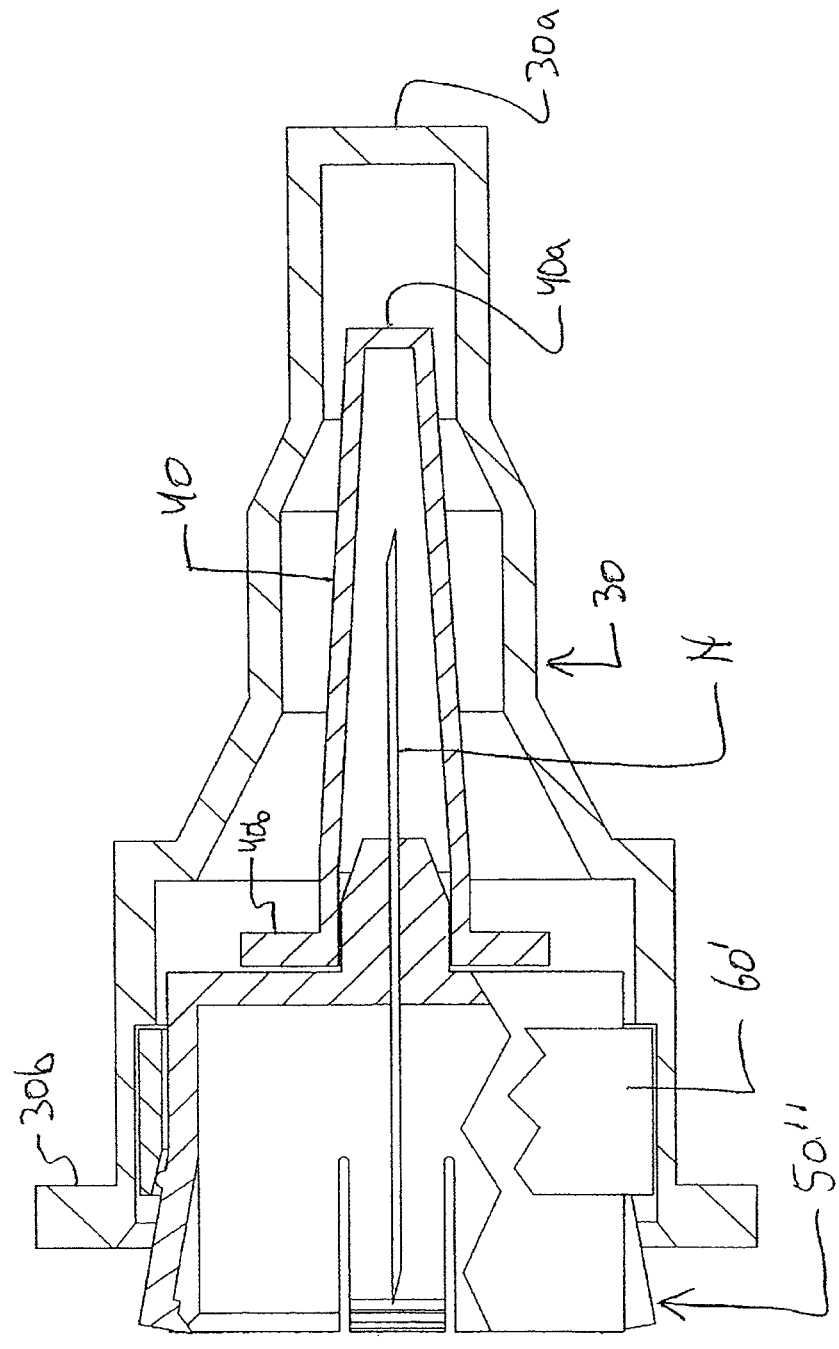
FIG. 34 shows a needle tip assembly according to still another embodiment of the invention. The needle tip assembly is shown in a position prior to installation onto the proximal end. The needle tip is shown in partial cross-section while the needle tip cap and the needle cap are shown in cross-section. Unlike the previous embodiments shown in FIGS. 8-32, this embodiment utilizes a ring which does not lock when moved to a position causing the inwardly projecting members to deflect inwardly.

FIG. 34 shows still another embodiment of a needle tip assembly. The needle tip assembly includes a needle tip cap 30 having various generally cylindrical portions with different diameters, a needle cap 40, and a needle tip $50^{II}$ of the type shown in FIGS. 29 and 30. As the needle tip cap 30 and the needle cap 40 of the instant embodiment are essentially identical to those used in previous embodiments, they have been accorded the same reference numerals. In this embodiment also, the proximal end 30a of the needle tip cap 30 is closed while the distal end includes a circumferential flange 30b. Similarly, the proximal end 40a of the needle cap 40 is closed while the distal end includes a circumferential flange 40b. The proximal end of the needle tip $50^{II}$ includes a needle N while the distal end includes an opening which is sized to allow the needle tip $50^{II}$ to be mounted to the threaded proximal end 2 of the pen needle device 1. In order to ensure that the needle tip $50^{II}$ is prevented from being re-installed onto the proximal end 2, the needle tip $50^{II}$ utilizes a ring 60' which can move axially from an initial position (similar to the position shown in FIG. 21) to a second position (similar to the position shown in FIG. 22) which causes the four inwardly deflecting members $50^{II}a$, $50^{II}b$, $50^{II}c$ and $50^{II}d$ to deflect inwards by an amount which is sufficient to prevent the needle tip $50^{II}$ (after being removed) from being re-installed onto the proximal end 2. As can be seen in FIG. 34, prior to the needle tip assembly being installed onto the threaded proximal end 2 (not shown in FIG. 34), the four inwardly deflecting members $50^{II}a$, $50^{II}b$, $50^{II}c$ and $50^{II}d$ are bent outwardly or deflected outwardly by an amount which is sufficient to allow the needle tip $50^{II}$ to be installed onto the proximal end 2 in the conventional manner, i.e., by axially sliding it on or by threading it on.

In a manner similar to that shown FIG. 21, the needle tip assembly of FIG. 34 can be installed onto the threaded proximal end 2 without activating the re-use prevention system or mechanism, i.e., without causing the ring 60' to move axially to the second or activated position. Accordingly, in the position shown in FIG. 34, the one or more inwardly deflecting members $50^{II}a$, $50^{II}b$, $50^{II}c$ and $50^{II}d$ are still bent outwardly or deflected outwardly by an amount which is sufficient to allow the needle tip $50^{II}$ to be installed onto the proximal end 2. Furthermore, while the ring 60' is in the position shown in FIG. 34, the needle tip assembly can be removed in the conventional way, e.g., by unthreading it off of the threaded end 2.

In the same way as was shown in FIG. 22, after the needle tip assembly shown in FIG. 34 is installed onto the threaded proximal end 2 (similar to that shown in FIG. 21), the needle tip cap 30 can be further moved axially in the distal direction (as indicated by the arrow in FIG. 22) to the point that it activates the re-use prevention system or mechanism, i.e., it causes the ring 60' to move axially in the distal direction until it assumes the second or activated position. Unlike the previous embodiments which provide for a locking position, i.e., characterized by engagement between the projections of the inwardly deflecting members and the inner circumferential recess of the ring, this embodiment utilizes projections on the members $50^{II}a$, $50^{II}b$, $50^{II}c$ and $50^{II}d$, but does not utilize the recess for receiving the same on the ring 60'. Instead, the ring 60' merely frictionally engages with the projections of the members $50^{II}a$, $50^{II}b$, $50^{II}c$ and $50^{II}d$ (thereby causing the members $50^{II}a$, $50^{II}b$, $50^{II}c$ and $50^{II}d$ to deflect inwardly to a greater extent than would be the case without the projections) when it is moved to the second or activated position. In order to ensure that the ring 60' does not move back to the original position (after being moved to the second position), the inner circumferential surface of the ring 60' and the projections of the members $50^{II}a$, $50^{II}b$, $50^{II}c$ and $50^{II}d$ can be provided with high friction surfaces such as e.g., a knurl, a high friction coating, etc. Although not shown, when the ring 60' is moved to the second or activated position, the inwardly deflecting members $50^{II}a$, $50^{II}b$, $50^{II}c$ and $50^{II}d$ will be deflected inwardly (as was the case in the previous embodiments) so that they will biased against the proximal end 2 and frictionally engage the threads thereof when the needle tip $50^{II}$ is unthreaded.

As was the case in the previous embodiments, once the needle tip assembly shown in FIG. 34 is installed and the re-use prevention system activated, the needle tip cap 30 can be removed by sliding it off axially. Then, the needle cap 40 can also be removed axially. Once the pen needle device with the installed needle tip assembly of FIG. 34 has been used to perform an injection, the needle tip $50^{II}$ can be removed in the following ways: one could simply grip the needle tip $50^{II}$ in the area of the ring 60' and unthread it from the threaded proximal end 2. This is risky, of course, because the user can be inadvertently be pricked by the exposed needle N; one could re-install the needle cap 40 and then grip the needle tip $50^{II}$ in the area of the ring 60' and unthread it from the threaded proximal end 2; one could re-install both the needle cap 40 and the needle tip cap 30, and then grip the needle tip cap 30 in the area just in front of the flange 30b and thereafter unthread the entire needle tip assembly thereby causing the needle tip $50^{II}$ to become unthreaded from the threaded proximal end 2; and one could re-install only the needle tip cap 30, and then grip the needle tip cap 30 in the area just in front of the flange 30b and thereafter unthread the needle tip assembly (without the cap 40) thereby causing the needle tip $50^{II}$ to become unthreaded from the threaded proximal end 2. As was the case in the previous embodiments, all of these ways are contemplated by the invention for this embodiment, with, however, the first way being the least desirable.

As was the case in the embodiment shown in FIGS. 20-28, once the needle tip $50^{II}$ is removed from the threaded proximal end 2 (and because the ring 60' has been moved to the activated position), the plurality of inwardly deflecting members $50^{II}a$, $50^{II}b$, $50^{II}c$ and $50^{II}d$ are caused to move inwardly to the point that they will not permit (i.e., they will interfere with) re-installation of the needle tip $50^{II}$ back onto the threaded proximal end 2 of the pen needle device 1. This occurs in substantially the same way as was shown in FIG. 28 which shows how the plurality of inwardly deflecting members have been moved inwardly to the point that they will not permit (i.e., they will interfere with) re-installation of the needle tip $50^{II}$ back onto the threaded proximal end 2 of the pen needle device 1 owing to the fact that they effectively reduce the diameter of the distal opening of the needle tip $50^{II}$.

Although not shown, the embodiment shown in FIG. 34 can, like the previous embodiments, utilize the needle tip cap shown in FIGS. 47-49 instead of the needle tip cap 30 shown in FIG. 34. Of course, the needle tip cap 30 can also have any desired configuration provided that it functions for its intended purpose, and can even be dispensed with without leaving the scope of the invention. In the later case, only the needle cap 40 (or even one of the type shown in FIGS. 53 and 54) would need to be utilized (for safety reasons) and the user could activate the re-use prevention system by gripping the ring 60' and sliding it distally until it assumes the activated position.

FIG. 35 shows still another embodiment of a needle tip assembly. The needle tip assembly includes a needle tip cap 30 having various generally cylindrical portions with different diameters, a needle cap 40, and a needle tip $50^{III}$ of the type shown in FIG. 33. As the needle tip cap 30 and the needle cap 40 of the instant embodiment are essentially identical to those used in the previous embodiments, they have been accorded the same reference numerals. In this embodiment also, the proximal end 30a of the needle tip cap 30 is closed while the distal end includes a circumferential flange 30b. Similarly, the proximal end 40a of the needle cap 40 is closed while the distal end includes a circumferential flange 40b. The proximal end of the needle tip $50^{III}$ includes a needle N while the distal end includes an opening which is sized to allow the needle tip $50^{III}$ to be mounted to the threaded proximal end 2 of the pen needle device 1. In order to ensure that the needle tip $50^{III}$ is prevented from being re-installed onto the proximal end 2, the needle tip $50^{III}$ utilizes a ring 60" which can move axially from an initial position (similar to the position shown in FIG. 21) to a second position (similar to the position shown in FIG. 22) which causes the four inwardly deflecting members $50^{III}a$, $50^{III}b$, $50^{III}c$ and $50^{III}d$ to deflect inwards by an amount which is sufficient to prevent the needle tip $50^{III}$ (after being removed) from being re-installed onto the proximal end 2. As can be seen in FIG. 35, prior to the needle tip assembly being installed onto the threaded proximal end 2 (not shown in FIG. 35), the four inwardly deflecting members $50^{III}a$, $50^{III}b$, $50^{III}c$ and $50^{III}d$ are bent outwardly or deflected outwardly by an amount which is sufficient to allow the needle tip $50^{III}$ to be installed onto the proximal end 2 in the conventional manner, i.e., by axially sliding it on or by threading it on.

In a manner similar to that shown FIG. 21, the needle tip assembly of FIG. 35 can be installed onto the threaded proximal end 2 without activating the re-use prevention system or mechanism, i.e., without causing the ring 60" to move axially to the second or activated position. Accordingly, in the position shown in FIG. 35, the one or more inwardly deflecting members $50^{III}a$, $50^{III}b$, $50^{III}c$ and $50^{III}d$ are still bent outwardly or deflected outwardly by an amount which is sufficient to allow the needle tip $50^{III}$ to be installed onto the proximal end 2. Furthermore, while the ring 60" is in the position shown in FIG. 35, the needle tip assembly can be removed by e.g., sliding or threading it off of the threaded end 2.

In the same way as was shown in FIG. 22, after the needle tip assembly shown in FIG. 35 is installed onto the threaded proximal end 2 (similar to that shown in FIG. 21), the needle tip cap 30 can be further moved axially in the distal direction (as indicated by the arrow in FIG. 22) to the point that it activates the re-use prevention system or mechanism, i.e., it causes the ring 60" to move axially in the distal direction until it assumes the second or activated position. Unlike the previous embodiments which provide for a locking position, i.e., characterized by engagement between the projections of the inwardly deflecting members and the inner circumferential recess of the ring, this embodiment utilizes no projections on the members $50^{III}a$, $50^{III}b$, $50^{III}c$ and $50^{III}d$ and does not therefore utilize the recess for receiving the same on the ring 60". Furthermore, unlike the embodiment shown in FIG. 33, the ring 60" of this embodiment utilizes no inner tapered section. Instead, the ring 60" merely frictionally engages with the outer surfaces of the members $50^{III}a$, $50^{III}b$, $50^{III}c$ and $50^{III}d$ when it is moved to the second or activated position. In order to ensure that the ring 60" does not move back to the original position (after being moved to the second position), the inner circumferential surface of the ring 60" and the outer surface of the members $50^{III}a$, $50^{III}b$, $50^{III}c$ and $50^{III}d$ can be provided with high friction surfaces such as e.g., a knurl, a high friction coating, etc. Although not shown, when the ring 60" is moved to the second or activated position, the inwardly deflecting members $50^{III}a$, $50^{III}b$, $50^{III}c$ and $50^{III}d$ will be deflected inwardly (as was the case in the previous embodiments) so that they will biased against the proximal end 2 and frictionally engage the threads thereof when the needle tip $50^{III}$ is unthreaded.

As was the case in the previous embodiments, once the needle tip assembly shown in FIG. 35 is installed and the re-use prevention system activated, the needle tip cap 30 can be removed by sliding it off axially. Then, the needle cap 40 can also be removed axially. Once the pen needle device with the installed needle tip assembly has been used to perform an injection, the needle tip $50^{III}$ can be removed in the following ways: one could simply grip the needle tip $50^{III}$ in the area of the ring 60" and unthread it from the threaded proximal end 2. This is risky, of course, because the user can be inadvertently be pricked by the exposed needle N; one could re-install the needle cap 40 and then grip the needle tip $50^{III}$ in the area of the ring 60" and unthread it from the threaded proximal end 2; one could re-install both the needle cap 40 and the needle tip cap 30, and then grip the needle tip cap 30 in the area just in front of the flange 30b and thereafter unthread the entire needle tip assembly thereby causing the needle tip $50^{III}$ to become unthreaded from the threaded proximal end 2; and one could re-install only the needle tip cap 30, and then grip the needle tip cap 30 in the area just in front of the flange 30b and thereafter unthread the needle tip assembly (without the cap 40) thereby causing the needle tip $50^{III}$ to become unthreaded from the threaded proximal end 2. As was the case in the previous embodiments, all of these ways are contemplated by the invention for this embodiment, with, however, the first way being the least desirable.

As was the case in the embodiment shown in FIGS. 20-28, once the needle tip $50^{III}$ is removed from the threaded proximal end 2 (and because the ring 60" has been moved to the activated position), the plurality of inwardly deflecting members $50^{III}a$, $50^{III}b$, $50^{III}c$ and $50^{III}d$ are caused to move inwardly to the point that they will not permit (i.e., they will interfere with) re-installation of the needle tip $50^{III}$ back onto the threaded proximal end 2 of the pen needle device 1. This occurs in substantially the same way as was shown in FIG. 28 which shows how the plurality of inwardly deflecting members have been moved inwardly to the point that they will not permit (i.e., they will interfere with) re-installation of the needle tip $50^{III}$ back onto the threaded proximal end 2 of the pen needle device 1 owing to the fact that they effectively reduce the diameter of the distal opening of the needle tip $50^{III}$.

Although not shown, the embodiment shown in FIG. 35 can, like the previous embodiments, utilize the needle tip cap shown in FIGS. 47-49 instead of the needle tip cap 30 shown in FIG. 33. Of course, the needle tip cap 30 can also have any desired configuration provided that it functions for its intended purpose, and can even be dispensed with without leaving the scope of the invention. In the later case, only the needle cap 40 (or even one of the type shown in FIGS. 53 and 54) would need to be utilized (for safety reasons) and the user could activate the re-use prevention system by gripping the ring 60" and sliding it distally until it assumes the activated position.

Figure 37:
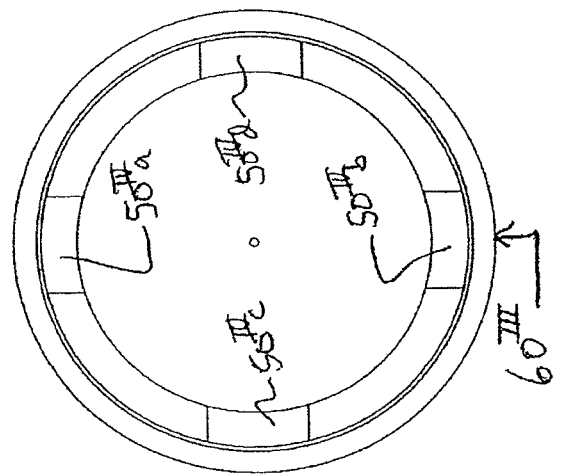
FIG. 37 shows a distal end view of a needle tip shown in FIG. 36.
Figure 36:
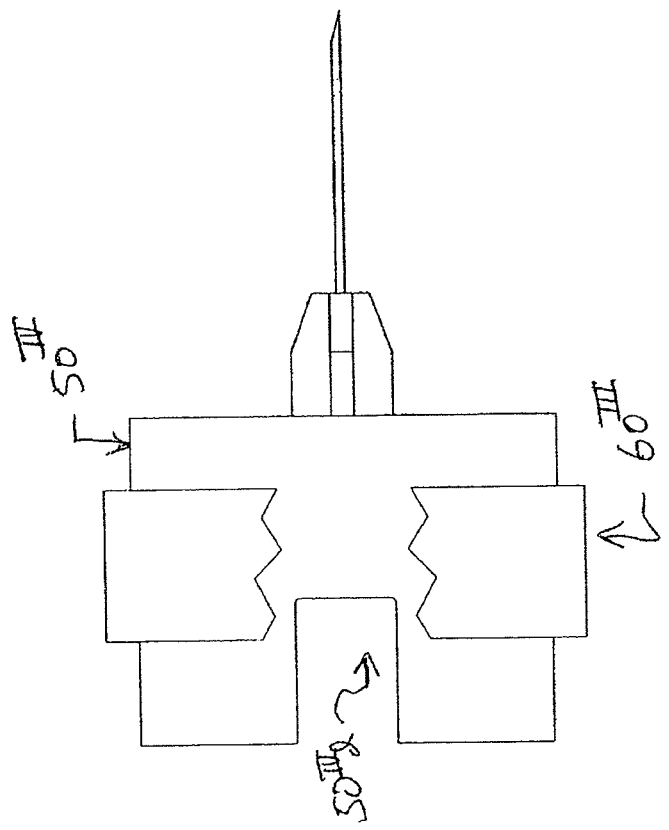
FIG. 36 shows a side view of a needle tip according to still another embodiment of the invention. The needle tip is shown in a position prior to installation onto the proximal end. Unlike the previous embodiments shown in FIGS. 8-32, this embodiment utilizes an elastic ring and a slotted distal end portion on the needle tip. That way, when the ring is moved towards the distal end, the ring causes the slotted distal end to compress or deflect inwardly.

FIGS. 36 and 37 show an optional needle tip $50^{IV}$ which can be used with any of the embodiments disclosed herein. Unlike the previous embodiments which utilize a essentially rigid or semi-rigid ring, this embodiment utilizes an elastic-type ring $60^{III}$; that is a ring which functions like an expanded rubber band that wants to contract. Indeed, the invention contemplates that the ring $60^{III}$ can be a rubber band ring or even a split spring metal ring which wants to contract but is kept expanded by virtue of being mounted to a portion of the body of the needle tip $50^{IV}$ which prevents its contraction. Furthermore, unlike the previous embodiments which utilize inwardly deflecting members which are caused to move inwardly by the ring, this embodiment utilizes four equally angularly spaced slots $50^{IV}a$, $50^{IV}b$, $50^{IV}c$, and $50^{IV}d$, which weakens the distal end of the needle tip $50^{IV}$ to the point that when, the ring $60^{III}$ is moved over the slots $50^{IV}a$, $5050^{IV}b$, $50^{IV}c$, and $50^{IV}d$, the distal end of the needle tip $50^{IV}$ will deflect inwardly to the point that it will not permit (i.e., it will interfere with) re-installation of the needle tip $50^{IV}$ back onto the threaded proximal end 2 of the pen needle device 1 owing to the fact that they effectively reduce the diameter of the distal opening of the needle tip $50^{IV}$. The needle tip $50^{IV}$, like the second embodiment, does not utilize any internal threads in the body of the needle tip $50^{IV}$ (i.e., the distal opening which receives therein the threaded proximal end 2 is generally cylindrical and smooth).

Figure 38:
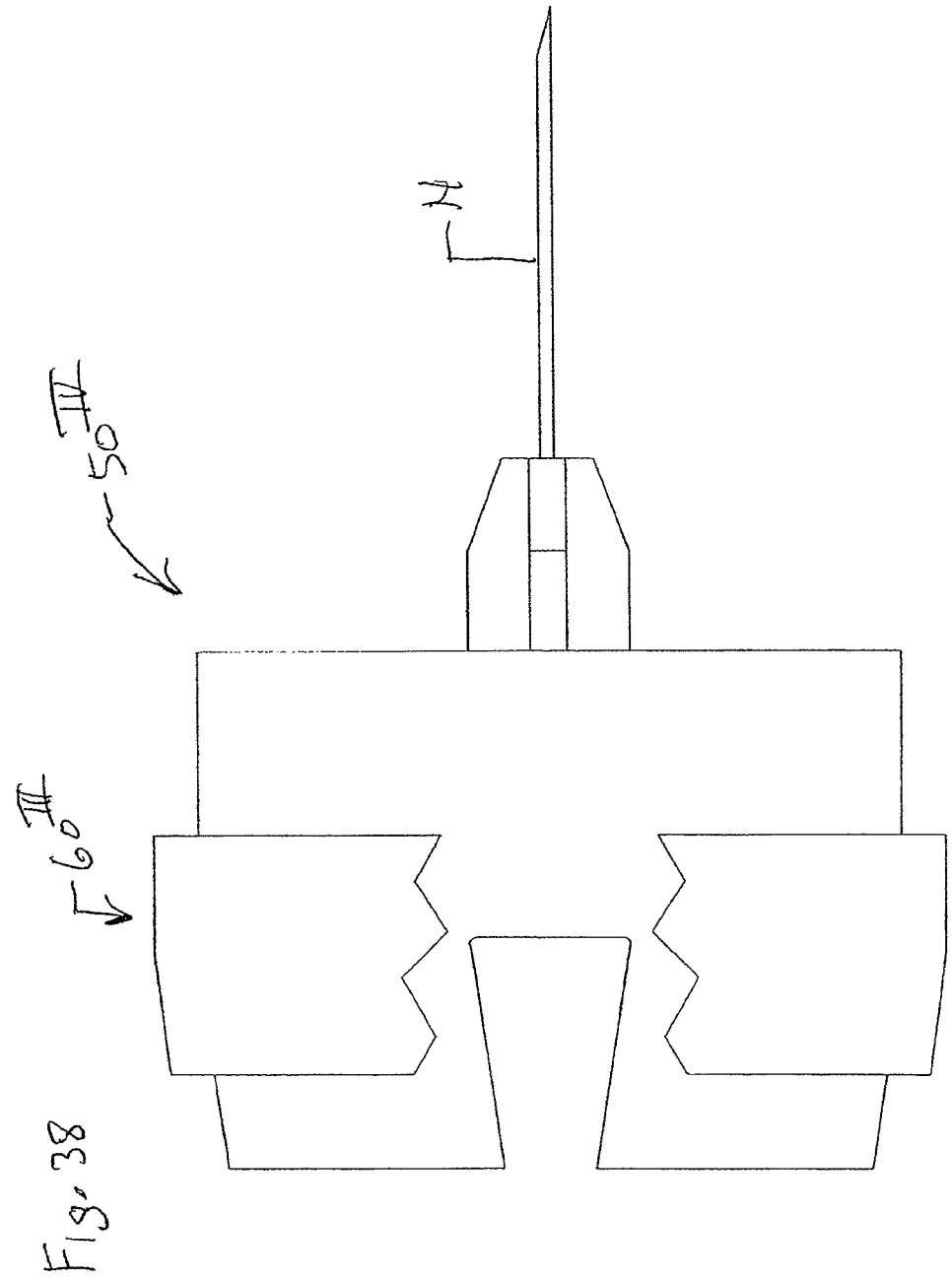
FIG. 38 shows a side view of a needle tip of FIG. 36 with the needle tip being in a position after removal from the proximal end. The ring has been moved towards the distal end causing the slotted distal end of the needle tip to compress or deflect inwardly and thereby prevent its re-installation.

As is evident from FIG. 38, once the needle tip $50^{IV}$ is removed from the threaded proximal end 2 (and because the ring $60^{III}$ has been moved to the activated position), the distal end of the needle tip $50^{IV}$ deflects inwardly to the point that it will not permit (i.e., will interfere with) re-installation of the needle tip $50^{IV}$ back onto the threaded proximal end 2 of the pen needle device 1. When this occurs, the distal end of the needle tip $50^{IV}$ effectively reduces the diameter of the distal opening of the needle tip $50^{IV}$.

FIGS. 39 and 40 show an optional needle tip $50^{V}$ which can be used with any of the needle tip assembly embodiments disclosed herein. The ring 60 can be, by way of non-limiting example, of the type described above in FIGS. 31 and 32. The needle tip $50^{V}$ can be, by way of non-limiting example, of the type described above in FIGS. 29 and 30, except that it additionally utilizes a plurality of, e.g., equally angularly spaced, guide/engaging projections $50^{V}e$ which are sized and configured to slide within correspondingly placed guide/engaging recesses 30'g arranged on the needle tip cap 30'. This embodiment similarly utilizes four equally angularly spaced members $50^V a$, $5050^V b$, $50^V c$ and $50^V d$, which can be moved inwardly by the ring 60 to the point that they will not permit (i.e., they will interfere with) re-installation of the needle tip $50^V$ back onto the threaded proximal end 2 of the pen needle device 1 owing to the fact that they effectively reduce the diameter of the distal opening of the needle tip $50^V$.

FIG. 40 shows a needle tip cap 30' which can be used with the needle tip $50^V$ shown in FIG. 39. The needle tip cap 30' is similar to the cap shown in FIGS. 18 and 19 except that it also utilizes e.g., equally angularly spaced, guide/engaging recesses 30'g which are sized and configured to slidably receive therein correspondingly placed guide/engaging projections $50^V e$ arranged on the needle tip $50^V$. The needle tip cap 30' has a closed proximal end 30'a, an open distal end having a circumferential flange 30'b, a distal opening 30'c sized to receive therein the ring 60, a shoulder 30'c which engages with a distal end of the ring 60 so as to cause the ring 60 to move to the locked position, a generally circumferential surface 30'e which is sized to slide over an outer surface of the needle tip $50^V$ and allow for engagement between guide/engaging projections $50^V e$ and guide/engaging recesses 30'g. Of course, the needle tip cap 30' can have any desired configuration provided that it functions for its intended purpose.

Figure 41:
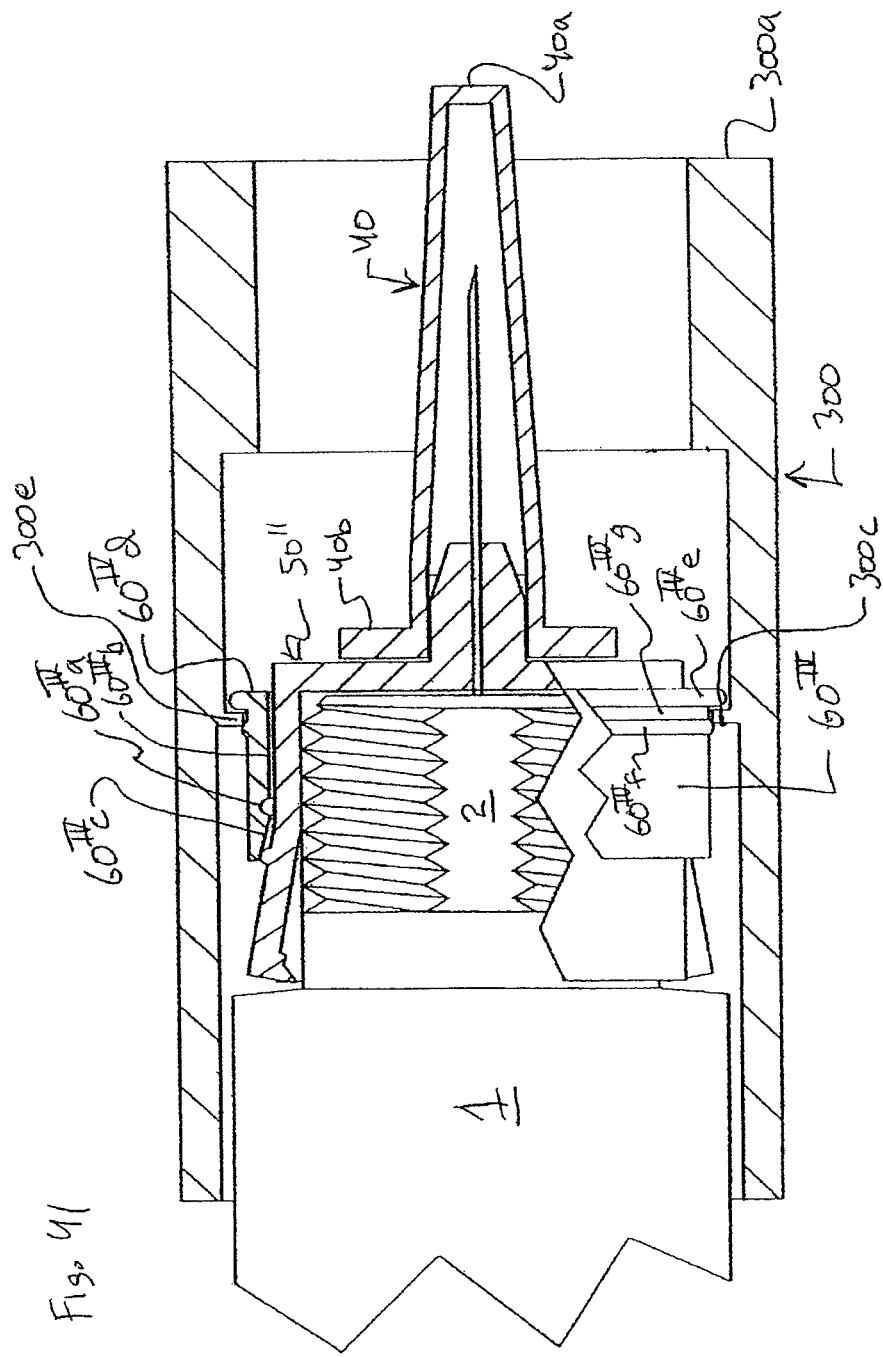
FIG. 41 shows a needle tip assembly according to still another embodiment of the invention. The needle tip assembly is shown in a position after being installed onto the proximal end of the pen needle injection device. The needle tip is shown in partial cross-section while the needle tip cap and the needle cap are shown in cross-section. Unlike the previous embodiments shown in FIGS. 8-40, this embodiment utilizes a needle tip cap that is slid over the proximal end of the pen needle device and remains on the device during injection. Furthermore, the ring includes a circumferential projection which acts to retain the needle tip cap in the position shown in FIG. 41.
Figure 42:
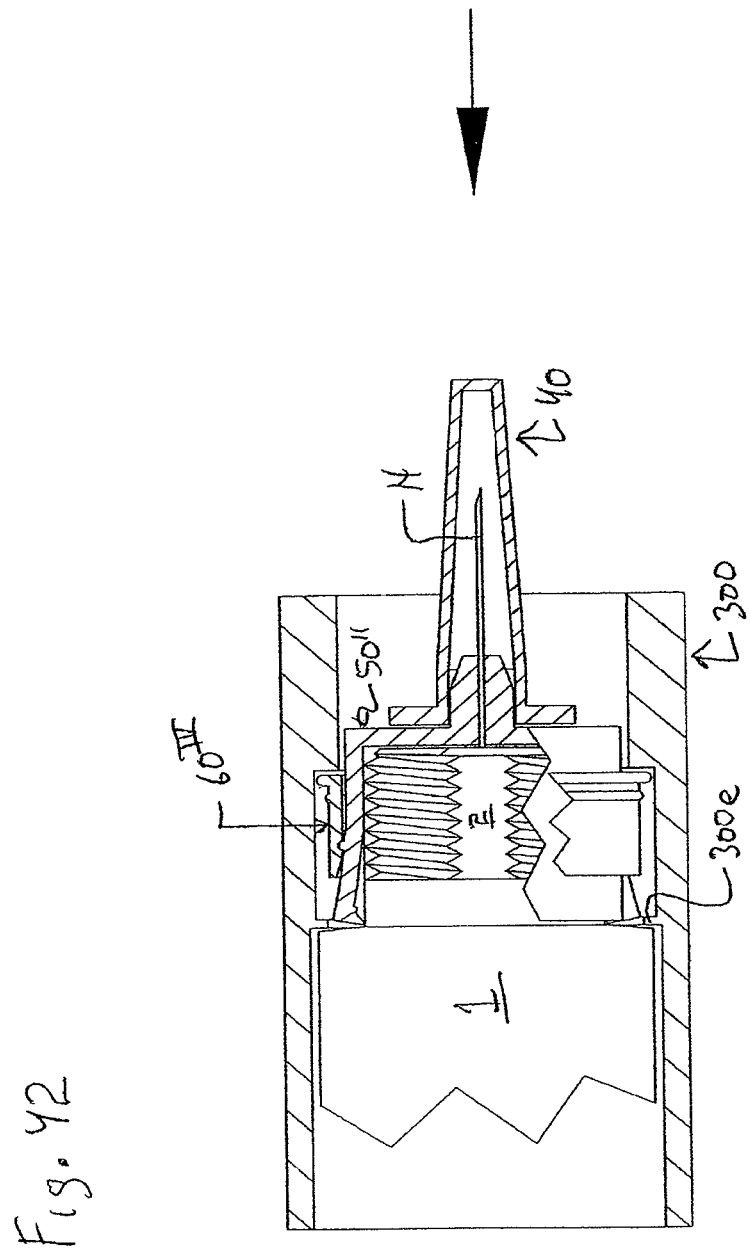
FIG. 42 shows the needle tip assembly of FIG. 41 after the needle tip cap is slid back to activate or move the ring to the locking position and also expose the needle and needle cap.
Figure 43:
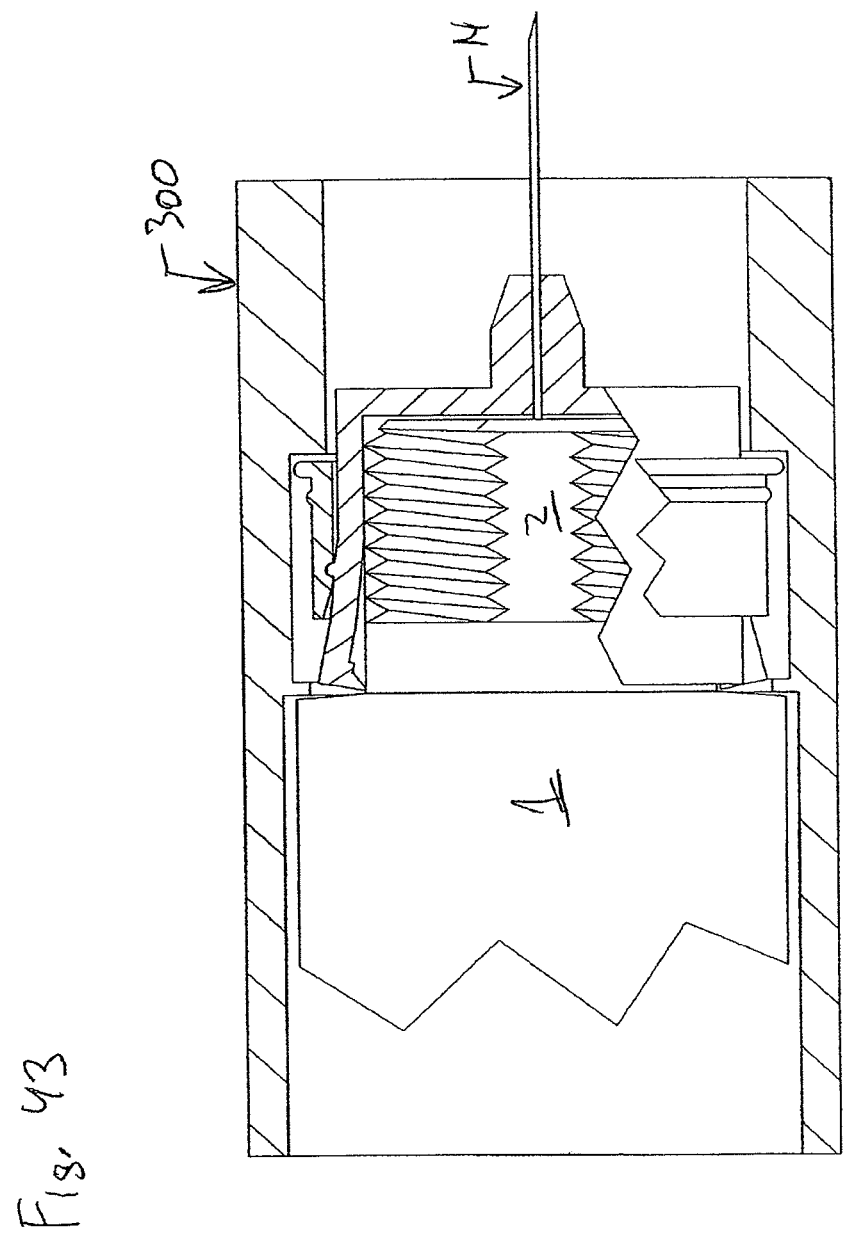
FIG. 43 shows the needle tip assembly of FIG. 42 after the needle cap is removed. As is shown in FIG. 43, the needle is now exposed and the pen needle device can now be used for injection.
Figure 44:
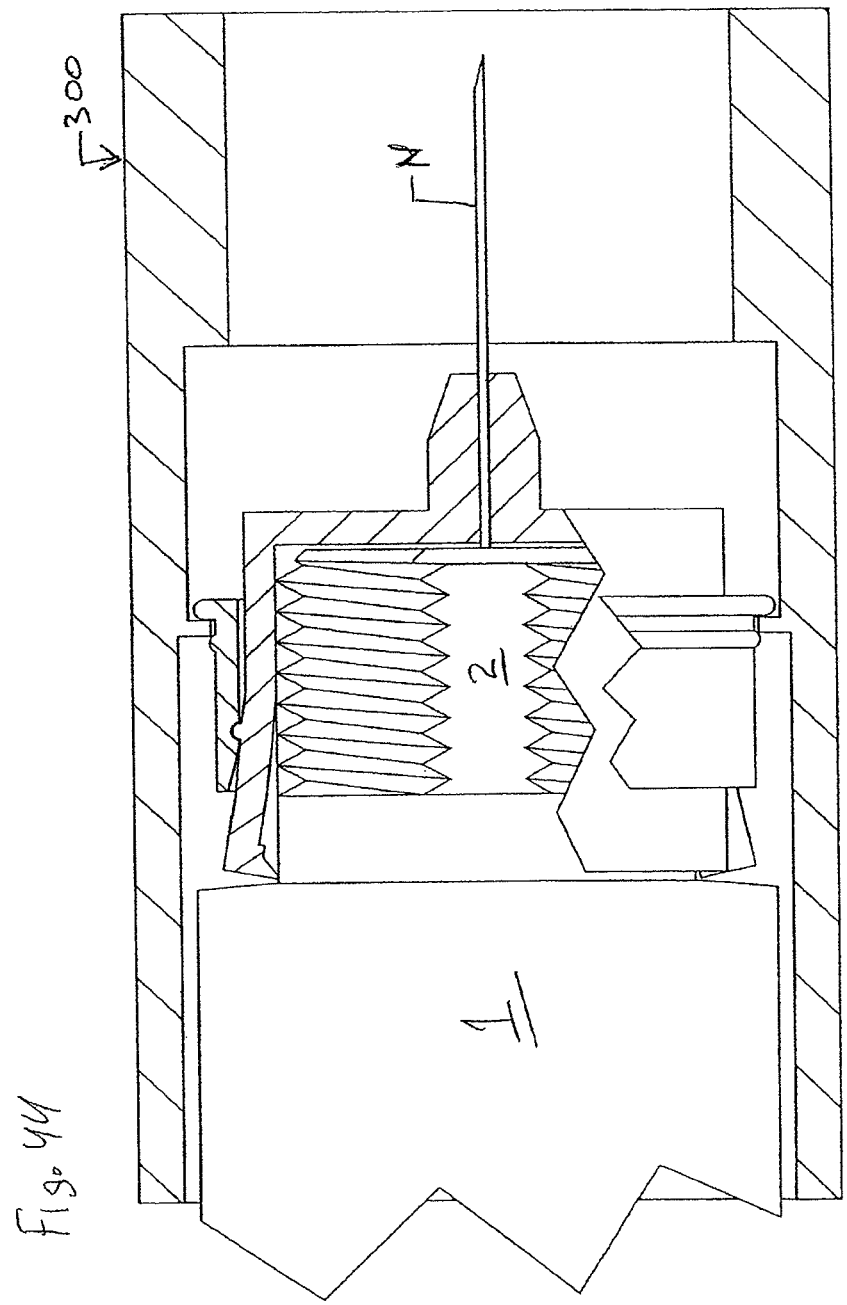
FIG. 44 shows the needle tip assembly of FIG. 43 after the needle tip cap is moved back to the original position shown in FIG. 41. As is shown in FIG. 44, the needle is now covered or protected by the needle tip cap.

FIGS. 41-44 show still another embodiment of a needle tip assembly. The needle tip assembly includes a needle tip cap 300 having a generally cylindrical configuration, a needle cap 40, and a needle tip $50^{II}$ of the type shown in FIGS. 29 and 30, and except that the ring $60^{IV}$ has a different configuration. In this embodiment, the ring $60^{IV}$ is generally cylindrical and has a proximal end $60^{IV} d$ which engages the shoulder 300c of the needle tip cap 300, a distal end having a tapered inner surface $60^{IV} c$ configured to facilitate sliding over the deflecting members $50"a/50"b/50"c/50"d$, a circumferential recess $60^{IV} a$ sized and configured to receive therein the projections P of the members $50"a/50"b/50"c/50"d$, and an inner cylindrical surface $60^{IV} b$ which is sized to slide over the needle tip body. Of course, the ring $60^{IV}$ can have any desired configuration provided that it functions for its intended purpose. Additionally, the ring $60^{IV}$ has a generally circumferential proximal flange $60^{IV} d$ which prevents the needle tip cap 300 from sliding off the ring $60^{IV}$ in the proximal direction. The ring $60^{IV}$ also has a generally circumferential retaining projection $60^{IV} f$ which ensures that the needle tip cap 300 is able to move the ring $60^{IV}$ in the distal direction so as to cause it to lock to the needle tip 50". However, after the ring $60^{IV}$ becomes locked to the needle tip 50", the projection $60^{IV} f$ will not be able to prevent further movement of the cap 300 and is, in fact, configured to allow (upon exertion of a predetermined force) the inwardly projecting circumferential projection 300e to pass over the projection 604 until the annular surface 300c of the projection 300e engages the proximal shoulder of the pen needle device 1. This is shown in FIG. 42. As the needle cap 40 of the instant embodiment is essentially identical to that used in the previous embodiment, it has been accorded the same reference numeral. In this embodiment, the proximal end 300a of the needle tip cap 300 is open (unlike the previous embodiments) while the distal end is configured to slide over the proximal portion of the device 1. Similarly, the proximal end 40a of the needle cap 40 is closed while the distal end includes a circumferential flange 40b. The proximal end of the needle tip $50^{II}$ includes a needle N while the distal end includes an opening which is sized to allow the needle tip $50^{III}$ to be mounted to the threaded proximal end 2 of the pen needle device 1. In order to ensure that the needle tip $50^{II}$ is prevented from being re-installed onto the proximal end 2, the needle tip $50^{III}$ utilizes the ring $60^{IV}$ which can move axially from an initial position (shown in FIG. 41) to a second or locked position (shown in FIG. 42) which causes the four inwardly deflecting members $50^{II} a$, $50^{II} b$, $50^{II} c$ and $50^{II} d$ to deflect inwards by an amount which is sufficient to prevent the needle tip $50^{II}$ (after being removed) from being re-installed onto the proximal end 2. As can be seen in FIG. 41, prior to activation, the four inwardly deflecting members $50^{II} a$, $50^{II} b$, $50^{II} c$ and $50^{II} d$ are bent outwardly or deflected outwardly by an amount which is sufficient to allow the needle tip $50^{II}$ to be installed onto the proximal end 2, i.e., by axially sliding it on or by threading it on.

As can be seen in FIG. 41, the needle tip assembly of FIG. 41 can be installed onto the threaded proximal end 2 without activating the re-use prevention system or mechanism, i.e., without causing the ring $60^{IV}$ to move axially to the second or activated position. Accordingly, in the position shown in FIG. 41, the one or more inwardly deflecting members $50^{II} a$, $50^{II} b$, $50^{II} c$ and $50^{II} d$ are still bent outwardly or deflected outwardly by an amount which is sufficient to allow the needle tip $50^{II}$ to be installed onto the proximal end 2. Furthermore, while the ring $60^{IV}$ is in the position shown in FIG. 41, the needle tip assembly can be removed, e.g., by sliding it off of the threaded end 2.

As is evident from FIG. 42, after the needle tip assembly shown in FIG. 41 is installed onto the threaded proximal end 2, the needle tip cap 300 can be further moved axially in the distal direction (as indicated by the arrow in FIG. 42) to the point that it activates the re-use prevention system or mechanism, i.e., it causes the ring $60^{IV}$ to move axially in the distal direction until it assumes the second or locked or activated position. Like many of the previous embodiments, locking occurs because of engagement between the projections of the inwardly deflecting members and the inner circumferential recess of the ring $60^{IV}$. This locking engagement also ensures that the ring $60^{IV}$ does not move back to the original position (after being moved to the second position) when the cap 300 is moved in the proximal direction to protect inadvertent contact with the needle N (see FIG. 44). As is evident from FIG. 42, when the ring $60^{IV}$ is moved to the second or activated position, the inwardly deflecting members $50^{II} a$, $50^{II} b$, $50^{II} c$, and $50^{II} d$ will be deflected inwardly (as was the case in the previous embodiments) so that they will biased against the proximal end 2 and frictionally engage the threads thereof when the needle tip $50^{II}$ is unthreaded.

Once the needle tip assembly shown in FIG. 41 is installed and the re-use prevention system activated (see FIG. 42), the needle tip cap 300 can be, after being in the position allowing it to be used for injection (see FIG. 43), slid in the proximal direction (see FIG. 44), but, unlike the previous embodiments, it is not removed. Then, the needle cap 40 can also be removed axially (in a manner similar to the previous embodiments). Once the pen needle device with the installed needle tip assembly has been used to perform an injection, the needle tip $50^{III}$ can be removed in the following way: one could re-install the needle cap 40 and then grip the needle tip cap 300 and slid it in the proximal direction until it assumes the position shown in FIG. 44; or one could simply grip the needle tip cap 300 and slid it in the proximal direction until it assumes the position shown in FIG. 44 without re-installing the needle cap 40. In either case, the user can then safely remove the entire needle tip assembly by either removing it axially or unthreading it axially. Of course, once removed, the needle tip assembly will be prevented from being re-installed because of the configuration of the ring $60^{IV}$ and $50''$. As was the case in the previous embodiments, all of these ways are contemplated by the invention for this embodiment.

Figure 53:
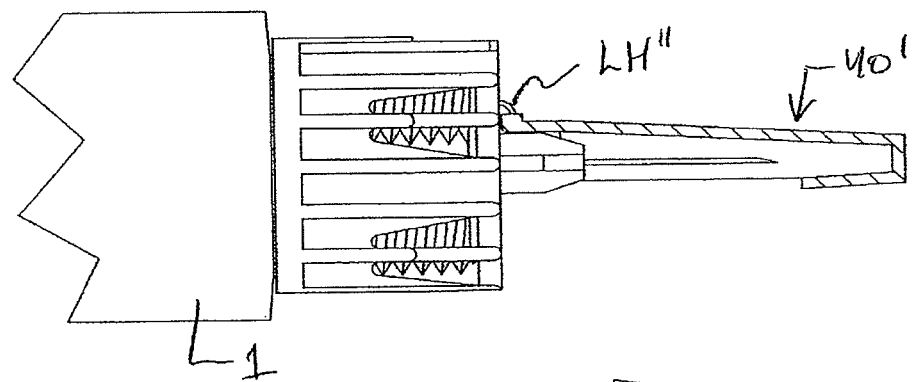
FIG. 53 shows the proximal end of FIG. 1 along with a needle tip assembly according to another embodiment of the invention. The needle tip is similar to that shown in the prior art FIGS. 1-7 except that the needle tip includes a needle cap member which is mounted to the needle tip body via a living hinge. The needle cap also includes a mechanism which allows the needle cap member to temporarily lock to the needle tip body. The needle cap is shown in cross-section.
Figure 54:
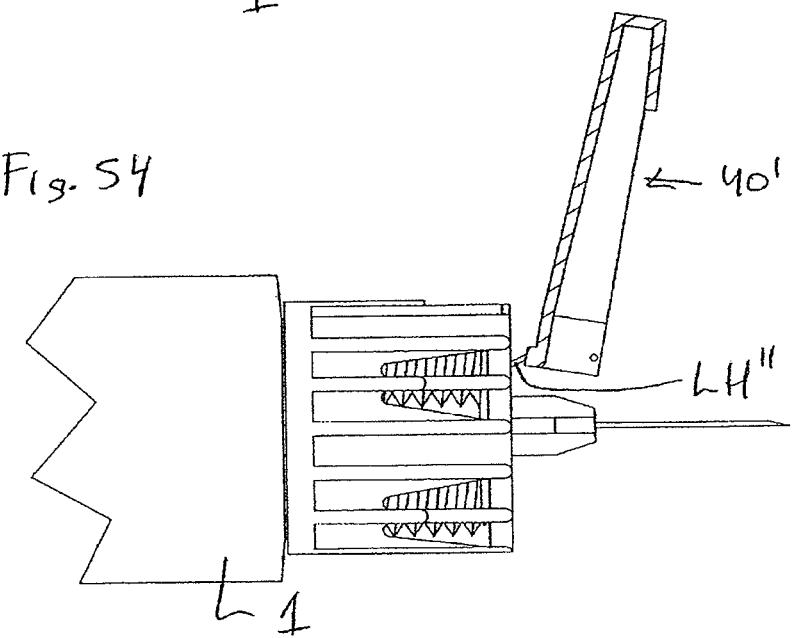
FIG. 54 shows the needle tip assembly of FIG. 53 after the needle cap is unlocked from the needle tip and been deflected distally. In this position, the needle tip can be used to perform an injection.

Although not shown, the embodiment shown in FIGS. 41-44 can, like the previous embodiments, utilize a needle cap of the type shown in FIGS. 53 and 54).

FIG. 45 shows a needle tip assembly according to still another embodiment of the invention. The needle tip assembly is substantially similar to that shown in FIGS. 41-44 except that it utilizes a coil compression spring S to bias the needle tip cap 300 in a proximal direction, i.e., towards the original position.

FIG. 46 shows still another embodiment of a needle tip $50^{VI}$ which can be used in one or more of the herein disclosed embodiments. The needle tip $50^{VI}$ can be utilized with a needle tip cap of the types disclosed herein or not with the former being preferred. A needle cap 40 (not shown) can also be utilized. The needle tip $50^{VI}$ can be substantially similar to the embodiment shown in FIGS. 29 and 30, except that it also includes a circumferential retaining shoulder RS which ensures that the ring $60^V$ is axially retained on the body of the needle tip $50^{VI}$. The proximal end of the needle tip $50^{VI}$ includes a needle N while the distal end includes an opening which is sized to allow the needle tip $50^{VI}$ to be mounted to the threaded proximal end 2 of the pen needle device 1. In order to ensure that the needle tip $50^{VI}$ is prevented from being re-installed onto the proximal end 2, the needle tip $50^{VI}$ utilizes a ring $60^V$ which can move axially from an initial position (similar to the position shown in FIG. 21) to a second or activated position (shown in FIG. 46) which causes the four inwardly deflecting members $50^{VI}a$, $50^{VI}b$, $50^{VI}c$, and $50^{VI}d$ to deflect inwards by an amount which is sufficient to prevent the needle tip $50^{VI}$ (after being removed) from being re-installed onto the proximal end 2. Although not shown, prior to the needle tip assembly being installed onto the threaded proximal end 2, the four inwardly deflecting members $50^{VI}a$, $50^{VI}b$, $50^{VI}c$, and $50^{VI}d$ are bent outwardly or deflected outwardly by an amount which is sufficient to allow the needle tip $50^{VI}$ to be installed onto the proximal end 2.

In the same way as was shown in FIG. 22, after the needle tip assembly shown in FIG. 46 is installed onto the threaded proximal end 2, the needle tip cap 30 (not shown) can be further moved axially in the distal direction to the point that it activates the re-use prevention system or mechanism, i.e., it causes the ring $60^V$ to move axially in the distal direction until it assumes the second or activated position shown in FIG. 46. Unlike the previous embodiments which provide for a locking position, i.e., characterized by engagement between the projections of the inwardly deflecting members and the inner circumferential recess of the ring, this embodiment utilizes projections on the members $50^{VI}a$, $50^{VI}b$, $50^{VI}c$, and $50^{VI}d$ and a recess in the ring $60^V$ for receiving the same, but does not provide for a locking engagement between these members. Instead, the inner recess of the ring $60^V$ merely frictionally engages with the projections of the members $50^{VI}a$, $50^{VI}b$, $50^{VI}c$, and $50^{VI}d$ when it is moved to the second or activated position. In order to ensure that the ring $60^V$ does not move back to the original position (after being moved to the second position), the inner circumferential surface of the ring $60^V$ and the outer surface of the members $50^{VI}a$, $50^{VI}b$, $50^{VI}c$, and $50^{VI}d$ can be provided with high friction surfaces such as e.g., a knurl, a high friction coating, etc. As shown in FIG. 46, when the ring $60^V$ is moved to the second or activated position, the inwardly deflecting members $50^{VI}a$, $50^{VI}b$, $50^{VI}c$, and $50^{VI}d$ are deflected inwardly (as was the case in the previous embodiments) so that they will biased against the proximal end 2 and frictionally engage the threads thereof when the needle tip $50^{VI}$ is unthreaded.

Once the re-use prevention system is activated (as shown in FIG. 46), the needle tip cap 30 (not shown) can be removed by sliding it off axially. Then, the needle cap 40 (not shown) can also be removed axially. Once the pen needle device with the installed needle tip assembly has been used to perform an injection, the needle tip $50^{VI}$ can be removed in the following ways: one could simply grip the needle tip $50^{VI}$ in the area of the ring $60^V$ and unthread it from the threaded proximal end 2. This is risky, of course, because the user can be inadvertently be pricked by the exposed needle N; one could re-install the needle cap 40 and then grip the needle tip $50^{VI}$ in the area of the ring $60^V$ and unthread it from the threaded proximal end 2; one could re-install both the needle cap 40 and the needle tip cap 30, and then grip the needle tip cap 30 in the area just in front of the flange 30b and thereafter unthread the entire needle tip assembly thereby causing the needle tip $50^{VI}$ to become unthreaded from the threaded proximal end 2; and one could re-install only the needle tip cap 30, and then grip the needle tip cap 30 in the area just in front of the flange 30b and thereafter unthread the needle tip assembly (without the cap 40) thereby causing the needle tip $50^{VI}$ to become unthreaded from the threaded proximal end 2. As was the case in the previous embodiments, all of these ways are contemplated by the invention for this embodiment, with, however, the first way being the least desirable.

As was the case in, e.g., the embodiment shown in FIGS. 20-28, once the needle tip $50^{VI}$ is removed from the threaded proximal end 2 (and because the ring $60^V$ has been moved to the activated position), the plurality of inwardly deflecting members $50^{VI}a$, $50^{VI}b$, $50^{VI}c$, and $50^{VI}d$ are caused to move inwardly to the point that they will not permit (i.e., they will interfere with) re-installation of the needle tip $50^{VI}$ back onto the threaded proximal end 2 of the pen needle device 1. This occurs in substantially the same way as was shown in FIG. 28 which shows how the plurality of inwardly deflecting members have been moved inwardly to the point that they will not permit (i.e., they will interfere with) re-installation of the needle tip $50^{VI}$ back onto the threaded proximal end 2 of the pen needle device 1 owing to the fact that they effectively reduce the diameter of the distal opening of the needle tip $50^{VI}$.

Although not shown, the embodiment shown in FIG. 46 can, like the previous embodiments, utilize the needle tip cap shown in FIGS. 47-49 instead of the needle tip cap 30. Of course, the needle tip cap 30 can also have any desired configuration provided that it functions for its intended purpose, and can even be dispensed with without leaving the scope of the invention. In the later case, only the needle cap 40 (or even one of the type shown in FIGS. 53 and 54) would need to be utilized (for safety reasons) and the user could activate the re-use prevention system by gripping the ring $60^V$ and sliding it distally until it assumes the activated position.

FIGS. 47-49 show an optional needle tip cap 3000 which can be used in one or more of the embodiments described herein. The needle tip cap 3000 can be similar to that shown in FIGS. 18 and 19 except that it utilize a two-piece folding connectable construction instead of the simple one-piece integral construction shown in FIGS. 18 and 19. In order to connect the two parts 3000A and 3000B, the cap 3000 utilizes a living hinge LH at one end and a lock system utilizing a lock member LM and a locking projection LP. This type of cap is advantageous because it allows the user to position the cap 3000 from the side instead of from the needle end. As a result, one can install the cap 3000 with a lower risk of being inadvertently punctured by the needle.

Figure 50:
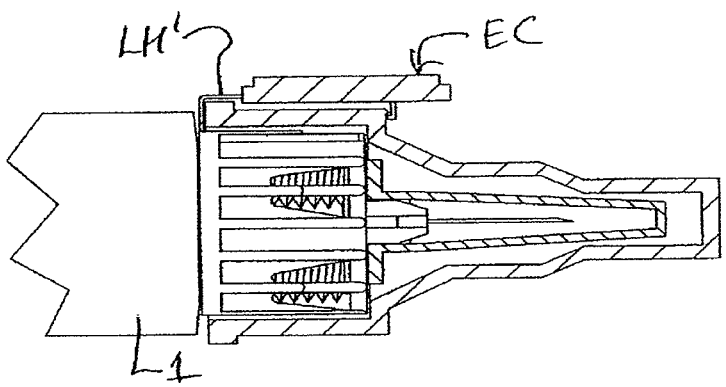
FIG. 50 shows the proximal end of FIG. 1 along with a needle tip assembly according to another embodiment of the invention. The needle tip assembly is similar to that shown in the prior art FIGS. 1-7 except that the needle tip includes a rear cap member which is mounted to the needle tip body via a living hinge. The needle tip cap also includes a mechanism which allows the rear cap member to temporarily lock thereto. The rear cap, needle tip cap and the needle cap are shown in cross-section.
Figure 51:
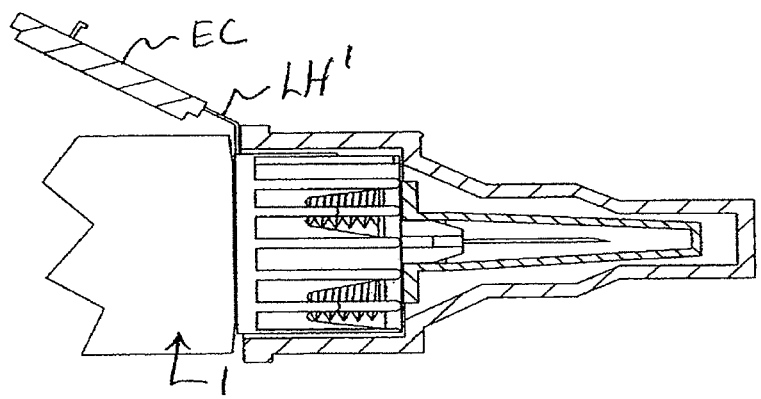
FIG. 51 shows the needle tip assembly of FIG. 50 after the rear end cap is unlocked from the needle tip cap and been deflected distally. In this position, the needle tip cap can then be removed in the manner shown in FIG. 4.
Figure 52:
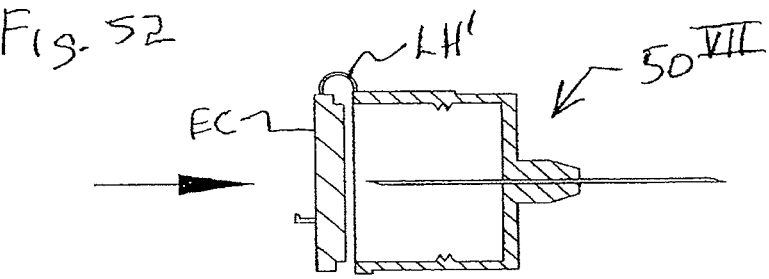
FIG. 52 shows the needle tip used in the embodiment shown in FIG. 50 and illustrates how the rear cap can be deflected via the living hinge to a position prior to covering the distal end of the needle tip.

FIGS. 50-52 show another non-limiting embodiment of a needle tip assembly which can be installed onto the proximal end of pen needle device 1. The needle tip assembly is similar to that shown in the prior art FIGS. 1-7 except that the needle tip $50^{VII}$ includes a rear end cap member EC which is mounted to the needle tip body via a living hinge LH'. The needle tip cap also includes a mechanism which allows the rear cap member EC to temporarily lock thereto. FIG. 51 shows the needle tip assembly of FIG. 50 after the rear end cap EC is unlocked from the needle tip cap and been deflected distally. In this position, the needle tip cap can then be removed in the manner shown in FIG. 4. FIG. 52 shows the needle tip $50^{VII}$ used in the embodiment shown in FIG. 50 and illustrates how the rear cap EC can be deflected via the living hinge LH' to a position prior to covering the distal end of the needle tip $50^{VII}$. The end cap EC can also be utilized in one or more of the embodiments disclosed herein.

FIG. 53 shows a needle tip assembly according to another embodiment of the invention. The needle tip is similar to that shown in the prior art FIGS. 1-7 except that the needle tip includes a needle cap member 40' which is mounted to the needle tip body via a living hinge LH". The needle cap also includes a mechanism which allows the needle cap member 40' to temporarily lock to the needle tip body. FIG. 54 shows the needle tip assembly of FIG. 53 after the needle cap 40' is unlocked from the needle tip and been deflected distally. In this position, the needle tip can be used to perform an injection.

FIGS. 55-57 show one non-limiting way in which a plurality of needle tip assemblies of either the prior art variety shown in FIGS. 2-7 or those of the invention described herein can be packaged in a housing H. The housing H performs the function of storing a number of needle tip assemblies and also functions as a tool for installing one needle tip assembly at a time onto the end of a pen needle. The housing H can be a generally cylindrical member with an open front end and a closed rear end. A plurality of spring retaining members RM can be arranged near the front open end. These members RM normally extend inwardly to prevent the needle tip assembly which is to be installed onto a pen needle from moving back into the housing H. Once in the position shown in FIG. 55, the user can grip the housing H and use it to force it onto the pen needle end 1. Of course, the user will first remove the removable sealing material layer (not shown) which is typically adhesively arranged on the open end of the needle tip cap, e.g., 3. Once the housing H is used to install one of the needle tip assemblies, the user can either leave the housing in the position shown in FIG. 56. Then, when the user desires to install a fresh needle tip assembly on the pen needle end 1, the user can slide the push button PB in the direction of the open end of the housing H until the next needle tip assembly reaches the position shown in FIG. 57. In this regard, the inwardly bent free ends of retaining members RM (a total of e.g., four, can be utilized) are designed to deflect outwardly in order to allow the next needle tip assembly to pass by. Installation can then occur in the same way as was described with regard to FIG. 55. Once, all of the needle tip assemblies, e.g., five, are utilized, the housing H can be discarded. As is evident from FIGS. 55-57, the push-button slides within an elongated slot SL formed in the side wall of the housing H and has an inner portion which is configured to engage and cause to move the needle tip assemblies arranged in series. Of course, the housing H can also have other configurations and can house as few as two or more than five assemblies.

The pen needle device described above can also utilize one or more features disclosed in the prior art documents expressly incorporated by reference herein. Furthermore, one or more of the various parts of the needle tip assembly can preferably be made as one-piece structures by e.g., injection molding, when doing so reduces costs of manufacture. Non-limiting materials for most of the parts include synthetic resins such as those approved for syringes or other medical devices. Furthermore, the invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

The invention claimed is:

1. A needle tip assembly for a pre-loaded syringe or a pen needle injection device, the needle tip assembly comprising:
   a body comprising a double-ended needle and being installable and removable from the pre-loaded syringe or pen needle injection device; and
   an outer safety member having a first portion that surrounds at least a portion of the body and a second portion that surrounds a skin puncturing end of the double-ended needle in an extended position, the outer safety member being axially movable to expose the skin puncturing end of the double-ended needle, wherein the needle tip assembly has the following modes of operation:
      a first mode where the needle tip assembly is installed on the pre-loaded syringe or pen needle injection device and the outer safety member is in the extended position;
      a second mode where the outer safety member is axially moved to a locking position and the skin puncturing end of the double-ended needle is caused to penetrate a skin surface; and
      a third mode where the outer safety member is returned to the extended position and the needle tip assembly is in a locked position preventing re-use.

2. The assembly of claim 1, wherein, in the third mode, the outer safety member is locked to the body via ring member.

3. The assembly of claim 1, wherein, in the third mode, the body is installed on the pre-loaded syringe or pen needle injection device.

4. The assembly of claim 1, wherein, in the third mode, the outer safety member is locked to the body via a projection that engages with a recess.

5. The assembly of claim 1, wherein the body is a one-piece body.

6. The assembly of claim 1, wherein the outer safety member is a one-piece body.

7. The assembly of claim 1, wherein the body comprises projections that are locked in position to prevent re-use of the needle tip assembly.

8. The assembly of claim 1, wherein the outer safety member has an axial length that is greater than an axial length of the body.

9. The assembly of claim 1, comprising a spring disposed about the skin puncturing end of the double-ended needle, the spring configured to bias the outer safety member toward the extended position.

10. A needle tip assembly for a pen needle injection device having a re-use prevention system, the needle tip assembly comprising:
    a. a needle tip removably connectable to one end of a pen needle injection device, where the needle tip comprises:
        i. a body having:
            1. a generally cylindrical sidewall; and
            2. an interior space sized to receive therein the one end of the pen needle injection device;
        ii. a needle having:
            1. a first puncturing end projecting beyond a forward end of the body; and
            2. a second puncturing end projecting into the interior space, the second puncturing end configured to extend into the one end of the pen needle injection device when the body is installed on the pen needle injection device; and
        iii. an axially moveable member mounted to the body, where the axially moveable member has a length that is less than a length of the body, and is configured to prevent re-use of the needle tip assembly when moved from a first position to a second position.

11. The needle tip assembly of claim 10, wherein the needle tip has projections configured to reduce a diameter of a distal end of the needle tip.

12. The needle tip assembly of claim 10, further comprising a safety cover non-removably coupled to the needle tip.

13. The needle tip assembly of claim 10, wherein the body comprises a threaded proximal end for engagement with the pen needle injection device.

14. The needle tip assembly of claim 10, further comprising a needle cap.

15. A method of installing a needle tip assembly on a pen needle injection device, comprising:
    prior to use during injection, installing a needle tip on one end of a pen needle injection device, the needle tip comprising:
        a body having an interior space sized to receive therein the one end of the pen needle injection device; and
        a needle having:
            a first puncturing end projecting beyond a forward end of the body; and
            a second puncturing end projecting into the interior space, the second puncturing end extending into the one end of the pen needle injection device when installed on the pen needle injection device;
    during injection with the first puncturing end, moving an axially moveable member mounted to the body from a first position to a second position thereby preventing reuse of the needle tip assembly; and
    after injection, removing the needle tip assembly from the one end of the pen needle injection device, the needle tip assembly locked to prevent reuse.

16. The method of claim 15, wherein the body has a generally cylindrical sidewall that surrounds at least a portion of the one end of the pen needle injection device when installed.

17. The method of claim 15, wherein the needle tip has projections configured to reduce a diameter of a distal end of the needle tip.

18. The method of claim 15, further comprising a safety cover non-removably coupled to the needle tip.

19. The method of claim 15, wherein the body comprises a threaded proximal end configured to engage with the one end of the pen needle injection device.

20. The method of claim 15, further comprising removing a needle cap from the needle tip assembly.

* * * * *